United States Patent
Anderson et al.

(10) Patent No.: US 12,000,809 B2
(45) Date of Patent: Jun. 4, 2024

(54) ZWITTERIONIC COMPOUNDS AS GAS CHROMATOGRAPHIC COLUMN STATIONARY PHASES

(71) Applicant: Iowa State University Research Foundation, Inc., Ames, IA (US)

(72) Inventors: Jared L. Anderson, Ames, IA (US); Kosuke Kuroda, Kanazawa (JP); He Nan, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 162 days.

(21) Appl. No.: 17/662,512

(22) Filed: May 9, 2022

(65) Prior Publication Data

US 2022/0268746 A1    Aug. 25, 2022

Related U.S. Application Data

(62) Division of application No. 16/229,962, filed on Dec. 21, 2018, now Pat. No. 11,353,435.

(60) Provisional application No. 62/675,927, filed on May 24, 2018.

(51) Int. Cl.
| | |
|---|---|
| *G01N 30/56* | (2006.01) |
| *B01D 15/36* | (2006.01) |
| *B01J 20/281* | (2006.01) |
| *C07D 233/60* | (2006.01) |
| *G01N 30/68* | (2006.01) |
| *G01N 30/72* | (2006.01) |
| *G01N 30/74* | (2006.01) |
| *G01N 30/02* | (2006.01) |

(52) U.S. Cl.
CPC ............. *G01N 30/56* (2013.01); *B01D 15/36* (2013.01); *C07D 233/60* (2013.01); *G01N 30/68* (2013.01); *G01N 30/72* (2013.01); *G01N 30/74* (2013.01); *G01N 2030/025* (2013.01); *G01N 2030/562* (2013.01)

(58) Field of Classification Search
CPC ........ G01N 30/56; G01N 30/68; G01N 30/72; G01N 30/74; G01N 2030/025; G01N 2030/562; G01N 2030/884; G01N 2030/889; B01D 15/36; C07D 233/60; B01J 20/281
See application file for complete search history.

(56) References Cited

PUBLICATIONS

Hu, W., "Electrostatic ion chromatography." Analytical chemistry 65.17 (1993): 2204-2208.*

Blahusiak et al., "Extraction of butyric acid with a solvent containing ammonium ionic liquid", Separation and Purification Technology, vol. 119, pp. 102-111, Sep. 16, 2013.
Bordes et al., "Room-Temperature Zwitterionic Ionic Liquids", French-Ukrainian Journal of Chemistry, vol. 04, Issue 01, pp. 85-94, 2016.
Delmonte et al., "Evaluation of highly polar ionic liquid gas chromatographic col. for the determination of the fatty acids in milk fat", Journal of Chromatography A, vol. 1233, pp. 137-146, Feb. 13, 2012.
Gao et al., "Temperature-responsive proton-conductive liquid crystals formed by the self-assembly of zwitterionic ionic liquids", Royal Society of Chemistry, vol. 5, pp. 63732-63737, Jul. 20, 2015.
Hallet et al., "Room-Temperature Ionic Liquids: Solvents for Synthesis and Catalysis. 2", Chemical Reviews, vol. 111, pp. 3508-3576, Apr. 6, 2011.
Kaminski et al., "Electrically induced liquid-liquid extraction from organic mixtures with the use of ionic liquids", Chemical Engineering Journal, vol. 235, pp. 109-123, Sep. 13, 2013.
Kollie et al., "Influence of Fluorine Substitution on the Solvation Properties of Tetraalkylammonium Alkanesulfonate Phases in Gas Chromatography", Chromatographia, vol. 33, No. 11/12, pp. 551-559, Jun. 1992.
Kuroda et al., "Design of Wall-Destructive but Membrane-Compatible Solvents", J. Am. Chem. Soc. vol. 139, pp. 16052-16055, Oct. 6, 2017.
Lu et al., "Lithium-Containing Zwitterionic Poly(Ionic Liquid)s as Polymer Electrolytes for Lithium-Ion Batteries", Journal of Physical Chemistry, vol. 121, pp. 17756-17763, Aug. 2, 2017.
Martak et al., "New Mechanism and Model of Butyric Acid Extraction by Phosphonium Ionic Liquid", J. Chem. Eng. Data, vol. 61, pp. 2979-2996, Jul. 26, 2016.
Poole et al., "Gas chromatography on wall-coated open-tubular columns with ionic liquid stationary phases", Journal of Chromatography A, vol. 1357, pp. 87-109, Mar. 18, 2014.
Reyhanitash et al., "Recovery of Volatile Fatty Acids from Fermented Wastewater by Adsorption", ACS Sustainable Chemistry & Engineering, vol. 5, pp. 9176-9184, Sep. 6, 2017.
Rocha et al., "Synthesis and Properties of Room-Temperature Choline Carboxylate Zwitterionic Ionic Liquids as Potential Electrolytes", ChemPlusChem, vol. 77, pp. 1106-1111, 2012.

(Continued)

*Primary Examiner* — John M Mauro

(74) *Attorney, Agent, or Firm* — McKee, Voorhees & Sease, PLC

(57) ABSTRACT

A gas chromatographic (GC) column using a zwitterionic compound and methods of use thereof are disclosed herein. The volatile free acids were observed to strongly retain on these zwitterionic compounds-based columns with excellent peak symmetry. By carefully tuning the structures of these zwitterionic compounds, different selectivity toward volatile free acids was demonstrated. These stationary phases possess a wide working range with thermal stabilities at higher temperatures.

8 Claims, 7 Drawing Sheets

(56) References Cited

PUBLICATIONS

Talebi et al., "Correction to: Branched-chain dicationic ionic liquids for fatty acid methyl ester assessment by gas chromatography", Analytical and Bioanalytical Chemistry, vol. 410, pp. 4763-4764, Jun. 4, 2018.

Tonova et al., "Hydrophobic 3-alkyl-1-methylimidazolium saccharinates as extractants for L-lactic acid recovery", Separation and Purification Technology vol. 125, pp. 239-246, Feb. 10, 2014.

Yoshizawa-Fujita et al., "Low-melting zwitterion: effect of oxyethylene units on thermal properties and conductivity", Chem. Commun., vol. 47, pp. 2345-2347, 2011.

* cited by examiner

ZWITTERIONIC COMPOUNDS AS GAS CHROMATOGRAPHIC COLUMN STATIONARY PHASES

CROSS-REFERENCE TO RELATED APPLICATIONS

This application is a divisional application of U.S. Ser. No. 16/229,962 filed Dec. 21, 2018, which claims the benefit of provisional application U.S. Ser. No. 62/675,927, filed May 24, 2018, both of which are herein incorporated by reference in their entirety.

GRANT REFERENCE

This invention was made with government support under Grant number CHE1709372 awarded by the National Science Foundation. The government has certain rights in the invention.

FIELD OF THE INVENTION

The present disclosure is related to a column using a zwitterionic compound as a stationary phase compound for chromatograph analysis or separation. Specifically, a gas chromatographic (GC) column with a zwitterionic compound possessing one or more cationic system and one or more sulfonate or phosphonate functional groups as stationary phases is disclosed for the GC analysis of volatile and polar organic molecules such as free acids (e.g., butyric acid, lactic acid formic acid, and acetic acid). The disclosed GC columns with the zwitterionic compounds exhibit exceptional separation performance towards volatile free acids. The free acids or other volatile organic molecules were observed to strongly retain with excellent peak symmetry on the GC columns with the disclosed zwitterionic compounds as stationary phases. Unique selectivity towards volatile free acids or other volatile organic molecules were demonstrated by tuning the structural features of the zwitterionic compounds.

BACKGROUND OF THE INVENTION

Volatile fatty acids (FAs) such as butyric acid and lactic acid are among the most important chemicals for the production of food, cosmetics, fuel, and pharmaceuticals. Gas chromatography (GC) is the most widely used method for the separation and quantification of individual fatty acids in any acylated lipids.

However, the highly polar and acidic nature of free acids limits choice of GC columns, which are all based on acid modified polyethylene glycol stationary phases.

Furthermore, FAs are typically converted to their methyl ester forms (FAMEs) before their analysis by GC coupled with either flame ionization or mass spectrometry detectors. Polar stationary phases such as polyethylene glycol (PEG) or cyanopropyl-modified polydimethylsiloxane (PDMS) have been most widely used for FAME analysis. For the analysis of FAs through FAMEs, the most widely used columns are HP-FFAP, Stabilwax-DA, and Nukol, which are all based on acid-modified PEG-based stationary phases.

Derivatization of FAs via various methods (e.g., acylation and alkylation) is typically necessary to increase the volatility of FAs as well as the feasibility of GC analysis. In addition, derivatization is also used to reduce analyte adsorption and improve peak separation and peak symmetry, since the carboxylic acid functional group often interacts strongly with the stationary phases, resulting in tailing peaks and often interfering with quantification.

However, the derivatization process for FAs' analysis can often be undesirable because it may lead to incomplete conversion, multiple by-products, and the introduction of side reactions. Therefore, more inert and selective GC stationary phases possessing high thermal stability for the direct analysis of FAs are desired.

Ionic liquids (IL) are a class of molten salts with melting points lower than 100° C. (Hallett, J. P.; Welton, T. *Chemical Reviews* 2011, 111, 3508-3576). IL-based GC stationary phases have been commercialized and successfully applied for the analysis of FAs (Poole, C. F.; Lenca, N. *Journal of Chromatography A* 2014, 1357, 87-109; Delmonte, P.; Fardin-Kia, A. R.; Kramer, J. K. G.; Mossoba, M. M.; Sidisky, L.; Tyburczy, C.; Rader, J. I. *Journal of Chromatography A* 2012, 1233, 137-146). These columns provide selectivity based on chain length, number of unsaturated units, and location or geometries (e.g., cis or trans) of the double bonds. Recently, twelve branched-chain di-cationic IL-based stationary phases have been developed and applied for the analysis of FAs and FAMEs (Talebi, M.; Patil, R. A.; Sidisky, L. M.; Berthod, A.; Armstrong, D. W. *Analytical and Bioanalytical Chemistry* 2017).

The structural modification of IL-based stationary phases results in different polarities and exhibited unique selectivity toward FAs. The solvation properties of these ILs revealed that retention of these analytes can be attributed to their strong hydrogen bonding accepting and donating abilities. In addition, ILs possessing high hydrogen bond basicity have been successfully used for the extraction of alcohols, alkaloids, and acids (e.g., butyric acid and methacrylic acid) (Blahušiak, M.; Schlosser, Š., Marták, J. *Separation and Purification Technology* 2013, 119, 102-111; Tonova, K.; Svinyarov, I.; Bogdanov, M. G. *Separation and Purification Technology* 2014, 125, 239-246; Reyhanitash, E.; Kersten, S. R. A.; Schuur, B. *ACS Sustainable Chemistry & Engineering* 2017, 5, 9176-9184; Kamiński, K.; Krawczyk, M.; Augustyniak, J.; Weatherley, L. R.; Petera, J. *Chemical Engineering Journal* 2014, 235, 109-123). The strong intermolecular interaction is attributed to the hydrogen bonds between the acid and IL anions (Marták, J.; Schlosser, Š. *Journal of Chemical & Engineering Data* 2016, 61, 2979-2996).

IL possessing methansulfonate anions (e.g., tetra-n-butylammonium methanesulfonate) were reported to possess high hydrogen bonding basicity values (Kollie, T. O.; Poole, C. F. *Chromatographia* 1992, 33, 551-559). However, ILs with methanesulfonate anions have rarely been investigated as GC stationary phases due to their high melting points (e.g., 75° C. to 80° C. for 1-butyl-3-methyl-imidazolium methanesulfonate). New structural motifs are needed to incorporate the methanesulfonate anion into ILs to improve the selectivity toward FAs, while meeting important requirements of IL-based stationary phases such as wide working ranges, inertness, and high thermal stability.

Accordingly, it is an objective of the present disclosure to provide a chromatographic column that uses a zwitterionic compound as stationary phase. The zwitterionic compound in the disclosed column has a low melting temperature and higher thermal stability and can be used as a stationary phase for chromatography columns. It is also an objective of the present disclosure to provide a GC column that uses classes of low melting zwitterionic compounds possessing sulfonate or phosphonate functional groups as stationary phases. It is also an objective of the present disclosure to provide a GC column comprising a zwitterionic compound for the selective separation and analysis of FAs or other volatile organic molecules. It is another objective of the present disclosure to provide a GC method for direct analysis of FAs.

BRIEF SUMMARY OF THE INVENTION

In one aspect, disclosed herein is a gas chromatographic (GC) column comprising a zwitterionic compound as its stationary phase, wherein the zwitterionic compound comprises one or more cationic systems and one or more anionic groups; wherein the one or more anionic groups comprise at least one sulfonate, phosphonate, or a group containing a sulfonate or phosphonate group; and wherein the cationic system is a quaternary ammonium, phosphonium, sulfonium compound, or a positively charged heterocyclic group derived from a 5 or 6 membered heterocyclic group having at least one nitrogen or sulfur atom.

In some embodiments, the cationic system comprises one or more cationic groups derived from a 5 or 6 membered heterocyclic molecule containing one or more nitrogen or sulfur atoms. In some other embodiments, the 5 or 6 membered heterocyclic molecule is an unsaturated, saturated, or partially saturated heterocyclic moiety with a positive charge.

In some embodiments, the zwitterionic compound in the disclosed gas chromatographic column has a formula:

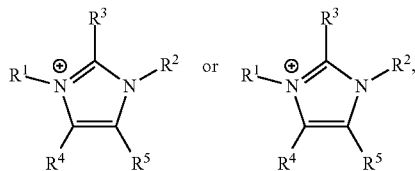

wherein $R^1$-$R^5$ are independently H, halogen, —NR'R", —NO$_2$, —COOR', —CHO, —OR', —PO$_3$R', —PO$_3$R'R", —SO$_2$, —SO$_3$R', —SR', substituted alkyl group, or unsubstituted alkyl group; wherein R' and R" are independently H or an alkyl group, and wherein at least one of $R^1$-$R^5$ comprises at least one anionic sulfonate, phosphonate, or a group containing a sulfonate or phosphonate group. In some other embodiments, one of $R^1$ and $R^2$ is a sulfonate, phosphonate, or a group containing a sulfonate or phosphonate group. In some other embodiments, one of $R^1$ and $R^2$ is a sulfonate, phosphonate, or a group containing a sulfonate or phosphonate group and $R^2$ or one of $R^3$, $R^4$, and $R^5$ is a nonionic alkyl group.

In another aspect, disclosed herein is a method of chromatographic analysis or separation, the method comprises separating an analyte by a column; wherein the column comprises a zwitterionic compound disclosed herein as its stationary phase.

In some embodiments, the column used in the disclosed method herein is one of the gas chromatographic columns disclosed herein. In some other embodiments, the column is at a temperature from about 0° C. to about 120° C.

In yet another aspect, disclosed herein is a method for GC analysis of a polar and volatile organic molecule, wherein the method comprises inputting a sample into a gas chromatographic column, wherein the column is one of the GC columns disclosed herein; and wherein the sample comprises a polar and volatile organic molecule.

The foregoing summary is illustrative only and is not intended to be in any way limiting. In addition to the illustrative aspects, embodiments, and features described above, further aspects, embodiments, and features will become apparent by reference to the drawings and the following detailed description.

Figure 1A:
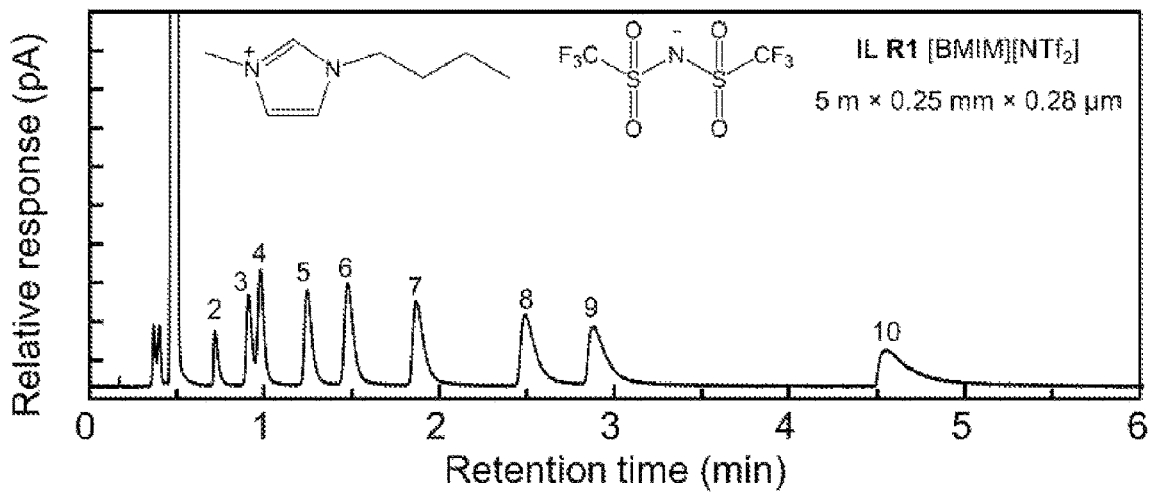
FIG. 1A, FIG. 1B, and FIG. 1C show the chromatographic separations of volatile acid mixture by the columns with IL R1, IL R2, and IL 3, respectively.

Various embodiments of the present disclosure will be described in detail with reference to the figures. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present disclosure shows a zwitterionic compound can be used as stationary phase for chromatographic column. Specifically, the present disclosure shows that a zwitterionic compound comprising one or more cationic systems and one or more sulfonates or phosphonates groups can be used as stationary phases in a gas chromatographic (GC) column. The present disclosure also demonstrates that a GC column with zwitterionic compounds possessing sulfonate functional groups as stationary phase can be used for free acid analysis.

The advantages for using a GC column with a zwitterionic compound as stationary phase include that some volatile compounds, such as free acids, can be retained on the column and analyzed with excellent peak symmetry, without the need of pre-analysis derivatization as in the prior art. The disclosed columns and methods offer a much-improved technique and method for analysis of free acids and other volatile organic compounds. Unique selectivity can be achieved by changing the structural features of the zwitterionic compounds. The solvation properties of these zwitterionic compound-based stationary phases can be evaluated for the first time using Abraham solvation parameter model. The analysis of free acids using the disclosed column is therefore faster and more accurate.

It is to be understood that all terminology used herein is for describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of the disclosure are presented in a range format. The description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosed columns and their methods of use pertain. Many methods and materials similar, modified, or equivalent to those described herein can be used in the practice of the embodiments of the disclosed columns and methods without undue experimentation. The preferred materials and methods are described herein. In describing and claiming the embodiments of the disclosed columns and methods, the following terminology will be used in accordance with the definitions set out below.

The term "about," as used herein, refers to variations in size, distance or any other types of measurements that can be resulted from the inherent heterogeneous nature of the measured objects and imprecise nature of the measurements themselves. The term "about" also encompasses variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods, and the like. The term "about" also encompasses amounts that differ due to different equilibrium conditions for a composition resulting from a particular initial mixture. Whether or not modified by the term "about", the claims include equivalents to the quantities.

The term "independently" means that where more than one substituent is selected from a number of possible substituents, those substituents may be the same or different.

As used herein, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are as defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having 2 to about 30 carbon atoms, and further including at least one double bond. In some embodiments, alkenyl groups have from 2 to about 20 carbon, or typically, from 2 to 10 carbon atoms. Alkenyl groups may be substituted or unsubstituted. Alkenyl groups may be substituted similarly to alkyl groups.

As used herein, the terms "alkylene", cycloalkylene", alkynylene, and alkenylene", alone or as part of another substituent, refer to a divalent radical derived from an alkyl, cycloalkyl, or alkenyl group, respectively, as exemplified by —$CH_2CH_2CH_2$—. For alkylene, cycloalkylene, alkynylene, and alkenylene groups, no orientation of the linking group is implied.

As used herein, "aryl" or "aromatic" groups are cyclic aromatic hydrocarbons that do not contain heteroatoms. Aryl groups include monocyclic, bicyclic, and polycyclic ring systems. Thus, aryl groups include, but are not limited to, phenyl, azulenyl, heptalenyl, biphenylenyl, indacenyl, florenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, in others from 6 to 12 or 6-10 carbon atoms in the ring portions of the groups. The phrase "aryl groups" includes groups containing fused rings, such as fused aromatic-aliphatic ring systems. Aryl groups may be substituted or unsubstituted.

As used herein, a "sulfonate" or "sulfonate group" is referred to a radical group by a general formula —$RSO_3H$ or its anion R—$SO_3^-$, wherein R is an alkyl, saturated/unsaturated, substituted/unsubstituted, straight/branched alkyl group.

As used herein, a "phosphonate" or "phosphonate group" is referred to a radical group by a general formula R—P(OR$^7$)$O_2$H or its anion R—P(OR$^7$)$O_2^-$, or R—$PO_3^{2-}$, wherein R is an alkyl, saturated/unsaturated, substituted/ unsubstituted, straight/branched alkyl group and $R^7$ is H, an alkyl, saturated/unsaturated, substituted/unsubstituted, straight/branched alkyl group.

As used herein, a "carboxylate" or "carboxylate group" is referred to a radical group by a general formula —RCOOH or its anion —RCOO$^-$, wherein R is an alkyl, saturated/unsaturated, substituted/unsubstituted, straight/branched alkyl group.

As used herein, R' and R" are independently H or an alkyl group.

As used herein, a "nonionic alkyl group" is referred to an alkyl group that contains no ionizable group or charged species under any pH value, therefore cannot become charges with pH changes. Similarly, a "nonionic group" is referred to a non-alkyl group that contains no ionizable group or charged species under any pH value, therefore cannot become charges with pH changes.

As used herein, "a group containing a —SO$_3$H, —PO$_3$H, or —COOH group" is referred to a radical group of —NR'R", —COOR', —OR', —PO$_3$R', —PO$_3$R'R", —SO$_3$R', —SR', non-alkyl group that contains one or more of a —SO$_3$H, —PO$_3$H, or —COOH group. Similarly, "a group containing a —SO$_3$H group" is referred to a radical group of —NR'R", —COOR', —OR', —PO$_3$R', —PO$_3$R'R", —SO$_3$R', —SR', or other non-alkyl group that contains one or more of a —SO$_3$H group; "a group containing a —PO$_3$H group" to a radical group of —NR'R", —COOR', —OR', —PO$_3$R', —PO$_3$R'R", —SO$_3$R', —SR', non-alkyl group that contains one or more of a —PO$_3$H group; and "a group containing a —COOH group" to a radical group of —NR'R", —COOR', —OR', —PO$_3$R', —PO$_3$R'R", —SO$_3$R', —SR', or other non-alkyl group that contains one or more of a —COOH group or its anion —COO$^-$.

As used herein, "a group containing a sulfonate, phosphonate, or carboxylate group" is referred to a radical group of —NR'R", —COOR', —OR', —PO$_3$R', —PO$_3$R'R", —SO$_3$R', —SR', non-alkyl group that contains one or more of a sulfonate, phosphonate, carboxylate group, or anion thereof. Similarly, "a group containing a sulfonate group" is referred to a radical group of —NR'R", —COOR', —OR', —PO$_3$R', —PO$_3$R'R", —SO$_3$R', —SR', or other non-alkyl group that contains one or more of a sulfonate group or its anion; "a group containing a phosphonate group" to a radical group of —NR'R", —COOR', —OR', —PO$_3$R', —PO$_3$R'R", —SO$_3$R', —SR', non-alkyl group that contains one or more of a phosphonate group or its anion; and "a group containing a carboxylate" to a radical group of —NR'R", —COOR', —OR', —PO$_3$R', —PO$_3$R'R", —SO$_3$R', —SR', or other non-alkyl group that contains one or more of a carboxylate group or its anion —COO$^-$.

As used herein, a "free acid" is referred to an $C_1$-$C_{15}$ organic acid that contains one or more —COOH groups and that has not been derivatized.

As used herein, a "volatile organic molecule" is referred to a $C_1$-$C_{15}$ organic molecule that can easily be evaporated at a temperature of about 0° C. to about 100° C. or room temperature. A volatile organic molecule can be an alkane, alkene, alkyne, ester, alkaloid, alcohol, acid, ether, aldehyde, amine, or aromatic.

As used herein, "Grob Test Mix" or "Grob Mix" is referred to a mixture of 12 compounds in methylene chloride for capillary GC testing. The ingredients and their concentrations in the mixture are (C10:0) Methyl caprate (110-42-9), 0.42 mg/mL; (C11:0) Methyl undecanoate (1731-86-8), 0.42 mg/mL; (C12:0) Methyl laurate (111-82-0), 0.41 mg/mL; (C10) Decane (124-18-5), 0.28 mg/mL; (C11) Undecane (1120-21-4), 0.29 mg/mL; 2,3-Butanediol (6982-25-8), 0.53 mg/mL; Dicyclohexylamine (101-83-7), 0.31 mg/mL; 2,6-Dimethylaniline (87-62-7), 0.32 mg/mL; 2,6-Dimethylphenol (576-26-1), 0.32 mg/mL; 2-Ethylhexanoic acid (149-57-5), 0.38 mg/mL; Nonanal (124-19-6), 0.40 mg/mL; and 1-Octanol (111-87-5), 0.36 mg/mL. This Grob Mix is commercially available.

Zwitterionic Compounds

Zwitterionic compounds or zwitterions are generally referred to neutral compounds having formal unit electrical charges of opposite sign. Sometime, zwitterionic compounds are restricted to compounds with the charges on non-adjacent atoms. Sometimes, zwitterionic compounds are referred to as inner salts, dipolar ions (a misnomer). Examples of typical zwitterionic compounds are $H_3N^+$ $CH_2C(=O)O^-$ ammoniaacetate (glycine), $(CH_3)_3N^+$—$O^-$ trimethylamine oxide.

Another exemplary group of zwitterionic compounds is one of zwitterionic surfactants. Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionic surfactants generally contain cationic and anionic groups which ionize to a nearly equal degree in the isoelectric region of the molecule and which can develop strong "inner-salt" attraction between positive-negative charge centers. Examples of such zwitterionic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxylate, sulfonate, sulfate, phosphate, or phosphonate. Betaine and sultaine surfactants are exemplary zwitterionic surfactants.

As used herein, a zwitterionic compound suitable for use in the present disclosure is a compound comprising one or more cationic systems and one or more anionic groups, wherein the one or more anionic groups comprise at least a sulfonate, phosphonate, or a group containing sulfonate or phosphonate group.

In some embodiments, a zwitterionic compound suitable for use in the present disclosure is a compound comprising one or more cationic system and one or more anionic groups, wherein the one or more anionic groups are sulfonate or phosphonate groups.

In some embodiments, a zwitterionic compound suitable for use in the present disclosure is a compound comprising two cationic systems and two anionic groups (a di-zwitterionic compound), wherein the two anionic groups comprise at least a sulfonate or phosphonate group.

As used herein, a cationic system is a quaternary ammonium, phosphonium, sulfonium compound, alkyl guanidinium, or a positively charged heterocyclic group derived from any of 5 or 6 membered heterocyclic groups having at least one nitrogen or sulfur atom in the heterocyclic ring. These 5 or 6 membered heterocyclic groups can be saturated, unsaturated, partially saturated, or substituted and can include two nitrogen atoms, three nitrogen atoms, 4 nitrogen atoms, other oxygen atom(s) in addition to one or more nitrogen or sulfur atoms.

The 5 or 6 membered heterocyclic groups including nitrogen or sulfur atom in the heterocyclic ring is well known in the art. The 5 or 6 membered heterocyclic groups include, but not limited to, pyrazole, imidazole, isoxazole, oxazole, isothiazole, thiazole, pyrrole, thiophene, azoline, azolidine, pyridazine, pyrimidine, pyrazine, and pyridine. The exemplary zwitterionic compounds that are suitable for use in the present disclosure and are derived from the 5 or 6 membered heterocyclic groups are

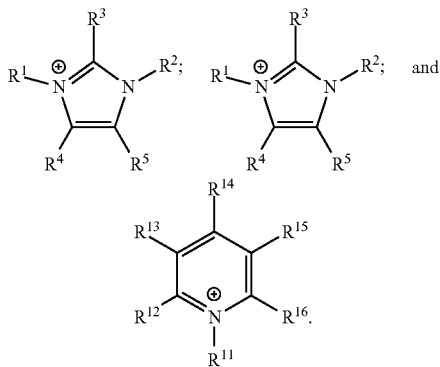

In the cationic system derived from a 5 or 6 membered heterocyclic group, the positive charge can be distributed among the atoms forming the heterocyclic ring or extended system with the substitution groups. In this disclosure, the positive charge may be drawn to be on one particular atom, but in reality, the positive charge may be in a resonance system and distributed among several atoms.

In some embodiments, the zwitterionic compound suitable for use in the present disclosure has a general structure of

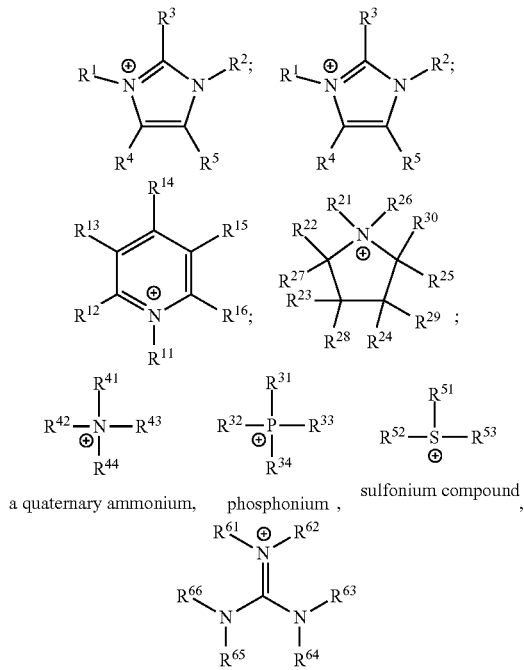

or mixture thereof, wherein at least one of $R^1$-$R^5$, $R^{11}$-$R^{16}$, $R^{21}$-$R^{30}$, $R^{31}$-$R^{34}$, $R^{41}$-$R^{44}$, $R^{51}$-$R^{53}$, and $R^{61}$-$R^{66}$, respec- tively, comprises at one sulfonate, phosphonate, or a group containing sulfonate or phosphonate group.

In the present disclosure, while it is possible that the two structures,

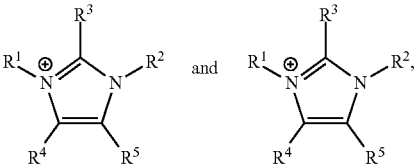

can be different because of the properties of $R^1$-$R^5$ groups, these two structures are considered to be equivalent because the positive charge is distributed among the atoms within the 5 member ring system or its possible extension to the substitution groups if they contains subsystem can extend the resonance system of the 5 member ring. In this disclosure, one of these two structures means another.

Similarly, the positive charge in

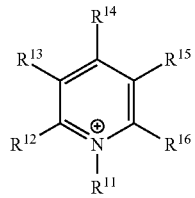

is distributed among the atoms within the 6 membered heterocyclic group or its possible extension.

As used herein, "substitution groups of a cationic system" are referred to the groups or atoms that directly attached the positively charged heterocyclic groups or positively charged N, P, or S atoms of the cationic systems of a zwitterionic compound. For examples, $R^1$-$R^5$, $R^{11}$-$R^{16}$, $R^{21}$-$R^{30}$, $R^{31}$-$R^{34}$, $R^{41}$-$R^{44}$, $R^{51}$-$R^{53}$, and $R^{61}$-$R^{66}$, respectively are the substitution groups of the respective cationic systems.

For a zwitterionic compound used in the disclosed GC column, one of the substitution groups in the zwitterionic compound comprises a sulfonate, phosphonate, or a group containing a sulfonate or phosphonate group. In some embodiments, this group is a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_8$-$C_{18}$, $C_{15}$-$C_{32}$, $C_{20}$-$C_{32}$, $C_{25}$-$C_{32}$, $C_2$-$C_{10}$, $C_5$-$C_{10}$, $C_{10}$-$C_{15}$, $C_{15}$-$C_{20}$, $C_{20}$-$C_{30}$, $C_{25}$-$C_{32}$ alkyl or non-alkyl group containing one or more sulfonate or phosphonate group(s). In some embodiments, this group is attached to the nitrogen or sulfur atom of the heterocyclic ring. In some other embodiments, this group is attached to a carbon atom of the heterocyclic group.

In some other embodiments, every nitrogen or sulfur atom in the heterocyclic group is attached with a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_{15}$-$C_{32}$, $C_{20}$-$C_{32}$, $C_{25}$-$C_{32}$, $C_2$-$C_{10}$, $C_5$-$C_{10}$, $C_8$-$C_{18}$, $C_{10}$-$C_{15}$, $C_{15}$-$C_{20}$, $C_{20}$-$C_{30}$, $C_{25}$-$C_{32}$ alkyl or non-alkyl group. In some embodiments, not every nitrogen or sulfur atom in the heterocyclic ring is attached with a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_{15}$-$C_{32}$, $C_{20}$-$C_{32}$, $C_{25}$-$C_{32}$, $C_2$-$C_{10}$, $C_5$-$C_{10}$, $C_8$-$C_{18}$, $C_{10}$-$C_{15}$, $C_{15}$-$C_{20}$, $C_{20}$-$C_{30}$, $C_{25}$-$C_{32}$ alkyl or non-alkyl group.

In some other embodiments, this group is a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_{15}$-$C_{32}$, $C_{20}$-$C_{32}$, $C_{25}$-$C_{32}$, $C_2$-$C_{10}$, $C_5$-$C_{10}$, $C_8$-$C_{18}$, $C_{10}$-$C_{15}$, $C_{15}$-$C_{20}$, $C_{20}$-

$C_{30}$, $C_{25}$-$C_{32}$ alkyl or non-alkyl group containing one or more sulfonate or phosphonate, the rest of substitution groups are H, —$CH_3$, —$CH_2CH_3$, or other unsubstituted or substituted alkyl group.

In some other embodiments, one group is a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_{15}$-$C_{32}$, $C_{20}$-$C_{32}$, $C_{25}$-$C_{32}$, $C_2$-$C_{10}$, $C_5$-$C_{10}$, $C_8$-$C_{18}$, $C_{10}$-$C_{15}$, $C_{15}$-$C_{20}$, $C_{20}$-$C_{30}$, $C_{25}$-$C_{32}$ alkyl or non-alkyl group containing one or more sulfonate or phosphonate group(s), one or more of the substitution groups is a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_{15}$-$C_{32}$, $C_{20}$-$C_{32}$, $C_{25}$-$C_{32}$, $C_2$-$C_{10}$, $C_5$-$C_{10}$, $C_8$-$C_{18}$, $C_{10}$-$C_{15}$, $C_{15}$-$C_{20}$, $C_{20}$-$C_{30}$, $C_{25}$-$C_{32}$ alkyl or non-alkyl group containing one or more sulfonate or phosphonate, or carboxylate group(s), the rest of substitution groups are is H, —$CH_3$, —$CH_2CH_3$, or other unsubstituted or substituted alkyl group. In some embodiments, when the zwitterionic compound contains two or more anionic groups, the zwitterionic compound may or may not contain additional cationic system in one or more of the substitution groups.

In some other embodiments, one group is a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_{15}$-$C_{32}$, $C_{20}$-$C_{32}$, $C_{25}$-$C_{32}$, $C_2$-$C_{10}$, $C_5$-$C_{10}$, $C_{10}$-$C_{15}$, $C_{15}$-$C_{20}$, $C_{20}$-$C_{30}$, $C_{25}$-$C_{32}$ alkyl or non-alkyl group containing one or more sulfonate or phosphonate group(s), one or more of the substitution groups is a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_{15}$-$C_{32}$, $C_{20}$-$C_{32}$, $C_{25}$-$C_{32}$, $C_2$-$C_{10}$, $C_5$-$C_{10}$, $C_{10}$-$C_{15}$, $C_8$-$C_{18}$, $C_{15}$-$C_{20}$, $C_{20}$-$C_{30}$, $C_{25}$-$C_{32}$ alkyl or non-alkyl group containing one or more sulfonate or phosphonate, or carboxylate group(s), the rest of substitution groups are H, —$CH_3$, —$CH_2CH_3$, or other unsubstituted or substituted alkyl group.

In some other embodiments, one of the substitution groups is a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_{15}$-$C_{32}$, $C_{20}$-$C_{32}$, $C_{25}$-$C_{32}$, $C_2$-$C_{10}$, $C_5$-$C_{10}$, $C_8$-$C_{18}$, $C_{10}$-$C_{15}$, $C_{15}$-$C_{20}$, $C_{20}$-$C_{30}$, $C_{25}$-$C_{32}$ alkyl or non-alkyl group containing one or more sulfonate or phosphonate group(s), one or more of the substitution groups is a $C_1$-$C_{32}$, $C_2$-$C_{32}$, $C_3$-$C_{32}$, $C_4$-$C_{32}$, $C_5$-$C_{32}$, $C_{10}$-$C_{32}$, $C_{15}$-$C_{32}$, $C_{20}$-$C_{32}$, $C_{25}$-$C_{32}$, $C_2$-$C_{10}$, $C_5$-$C_{10}$, $C_8$-$C_{18}$, $C_{10}$-$C_{15}$, $C_{15}$-$C_{20}$, $C_{20}$-$C_{30}$, $C_{25}$-$C_{32}$ nonionic alkyl or non-alkyl group, the rest of substitution groups are H, —$CH_3$, —$CH_2CH_3$, or other unsubstituted or substituted alkyl group.

In some embodiments, when any of the substitution group contains an amine or hydroxyl group, these kinds of groups can be further modified with a $R^7(OE)_nR^6$— group, $R^6$ is null, unsubstituted $C_1$-$C_{20}$ alkylene group, OE is —$OCH_2CH_2$—, —$OCH_2CH_2CH_2$—, —$OCH(CH_3)CH_2$—, or combination thereof, $R^7$ is H, —$CH_3$, —$CH_2CH_3$, or other unsubstituted or substituted alkyl group; and n is 1-50.

In some embodiments, the zwitterionic compound suitable for use in the present disclosure includes at least one cationic system or atom as shown in the structures above and at least one sulfonate, phosphonate, or a group containing sulfonate or phosphonate group in $R^1$-$R^5$, $R^{11}$-$R^{16}$, $R^{21}$-$R^{30}$, $R^{31}$-$R^{34}$, $R^{41}$-$R^{44}$, $R^{51}$-$R^{53}$, and $R^{61}$-$R^{66}$, respectively. In addition to the sulfonate or phosphonate group in one $R^1$-$R^{44}$, and $R^{51}$-$R^{53}$, respectively, one or more additional anionic group(s) can exist in the same group containing the first sulfonate or phosphonate group or in another one of $R^1$-$R^5$, $R^{11}$-$R^{16}$, $R^{21}$-$R^{30}$, $R^{31}$-$R^{34}$, $R^{41}$-$R^{44}$, $R^{51}$-$R^{53}$, and $R^{61}$-$R^{66}$, respectively. The additional anionic group(s) can be one or more of carboxylate, sulfonate, phosphonate, or a group containing sulfonate or phosphonate, or carboxylate group.

In some embodiments, the zwitterionic compound suitable for use in the present disclosure includes addition one or more cationic systems or atoms as in the structures shown above. The additional cationic system(s) can exist in the substitution groups of the first cationic system. For examples, additional cationic system can be part of the $R^1$-$R^5$, $R^{11}$-$R^{16}$, $R^{21}$-$R^{30}$, $R^{31}$-$R^{34}$, $R^{41}$-$R^{44}$, $R^{51}$-$R^{53}$, and $R^{61}$-$R^{66}$, respectively, in the exemplary structures shown above.

In some embodiments, at least one or some of $R^1$-$R^5$, $R^{11}$-$R^{16}$, $R^{21}$-$R^{30}$, $R^{31}$-$R^{34}$, $R^{41}$-$R^{44}$, $R^{51}$-$R^{53}$, and $R^{61}$-$R^{66}$, respectively, can be or comprise alkyl groups that can be straight or some of them are branched, saturated or unsaturated, substituted or unsubstituted, or combination thereof and some of them are independently H, halogen, —NR'R", —$NO_2$, —COOR', —CHO, —OR', —$PO_3R'$, $PO_3R'R''$, —$SO_3R'$, —$SO_2$, —$SO_3R'$, or —SR'; wherein R' and R" are independently H or an alkyl group.

In some embodiments, the zwitterionic compound suitable for use in the present disclosure can carried one or more positive or negative charge of the imbalanced cationic system/group and anionic group. The net charge(s) can be balanced by external cationic or anionic group(s).

An exemplary formula for the disclosed zwitterionic compounds is:

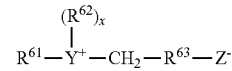

wherein $R^{61}$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^{62}$ is an alkyl or monohydroxy alkyl group containing 1 to 3 carbon atoms; x is 1 when Y is a sulfur atom and 2 when Y is a nitrogen or phosphorus atom, $R^{63}$ is an alkylene or hydroxy alkylene or hydroxy alkylene of from 1 to 4 carbon atoms and Z is a radical selected from the group consisting of sulfonate, phosphate groups, or a group containing a sulfonate or phosphonate group.

Examples of zwitterionic compounds having the structures listed above include: 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate.

In one aspect, disclosed herein is a gas chromatographic (GC) column comprising a zwitterionic compound as its stationary phase, wherein the zwitterionic compound comprises one or more cationic systems and one or more anionic groups; wherein the one or more anionic groups comprises at least one sulfonate, phosphonate, or a group containing a sulfonate or phosphonate group; and wherein the cationic system is a quaternary ammonium, phosphonium, sulfonium compound, or a positively charged heterocyclic group derived from a 5 or 6 membered heterocyclic group having at least one nitrogen or sulfur atom.

In some other embodiments, the cationic system comprises one or more cationic groups derived from a 5 or 6 membered heterocyclic molecule containing one or more nitrogen or sulfur atoms. In some other embodiments, the 5 or 6 membered heterocyclic molecule is an unsaturated, saturated, or partially saturated heterocyclic moiety with a positive charge.

In some embodiments, the cationic system comprises one or more cationic groups derived from pyrazole, imidazole, isoxazole, oxazole, isothiazole, thiazole, pyrrole, thiophene, azoline, azolidine, pyridazine, pyrimidine, pyrazine, pyridine, or combination thereof.

In some embodiments, the zwitterionic compound in the disclosed gas chromatographic column has a formula:

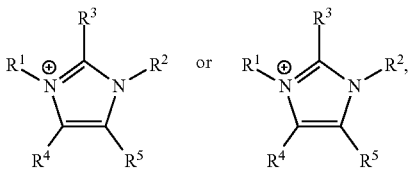

wherein $R^1$-$R^5$ are independently H, halogen, —NR'R", —NO$_2$, —COOR', —CHO, —OR', —PO$_3$R', PO$_3$R'R", —SO$_2$, —SO$_3$R', —SR', substituted alkyl group, or unsubstituted alkyl group; wherein R' and R" are independently H or an alkyl group, and wherein at least one of $R^1$-$R^5$ comprises at least one anionic sulfonate, phosphonate, or a group containing a sulfonate or phosphonate group. In some other embodiments, one of $R^1$ and $R^2$ is a sulfonate, phosphonate, or a group containing a sulfonate or phosphonate group. In some other embodiments, one of $R^1$ and $R^2$ is a sulfonate, phosphonate, or a group containing a sulfonate or phosphonate group and $R^2$ or one of $R^3$, $R^4$, and $R^5$ is a nonionic alkyl group.

In some embodiments, the zwitterionic compound in the disclosed gas chromatographic column has a formula:

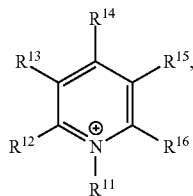

wherein $R^{11}$-$R^{16}$ are independently H, halogen, —NR'R", —NO$_2$, —COOR', —CHO, —OR', —PO$_3$R', PO$_3$R'R", —SO$_2$, —SO$_3$R', —SR', substituted alkyl group, or unsubstituted alkyl group; wherein R' and R" are independently H or an alkyl group, and wherein at least one of $R^{11}$-$R^{16}$ comprises a sulfonate, phosphonate, or a group containing sulfonate or phosphonate group. In some other embodiments, $R^{11}$ is a sulfonate, phosphonate, or a group containing sulfonate or phosphonate group. In yet some other embodiments, $R^{11}$ is a sulfonate, phosphonate, or a group containing a sulfonate or phosphonate group and another one of $R^{12}$-$R^{16}$ is a nonionic alkyl group.

In some embodiments, the zwitterionic compound has a formula:

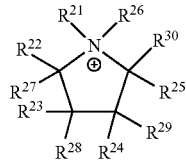

wherein $R^{21}$-$R^{30}$ are independently H, halogen, —NR'R", —NO$_2$, —COOR', —CHO, —OR', —PO$_3$R', PO$_3$R'R", —SO$_2$, —SO$_3$R', —SR', substituted alkyl group, or unsubstituted alkyl group; wherein R' and R" are independently H or an alkyl group; and wherein at least of one of $R^{21}$-$R^{26}$ comprises at least one anionic sulfonate, phosphonate, or a group containing a sulfonate or phosphonate group. In some other embodiments, one of $R^{21}$ and $R^{26}$ is a sulfonate, phosphonate, or a group containing a sulfonate or phosphonate group. In yet other embodiments, one of $R^{21}$ and $R^{26}$ is a sulfonate, phosphonate, or a group containing a sulfonate or phosphonate group and another one of $R^{21}$ and $R^{26}$ or one of $R^{22}$-$R^{25}$ and $R^{27}$-$R^{30}$ is nonionic alkyl group.

In some embodiments, the zwitterionic compound in the disclosed column has a formula:

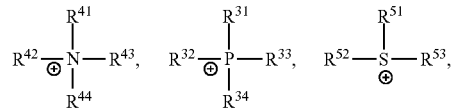

or mixture thereof, wherein $R^{31}$-$R^{34}$, $R^{41}$-$R^{44}$, and $R^{51}$-$R^{53}$, respectively, are independently H, halogen, —NR'R", —NO$_2$, —COOR', —CHO, —OR', —PO$_3$R', —PO$_3$R'R", —SO$_2$, —SO$_3$R', —SR', substituted alkyl group, or unsubstituted alkyl group; wherein R' and R" are independently H or an alkyl group, and wherein at least one of $R^{31}$-$R^{34}$, $R^{41}$-$R^{44}$, and $R^{51}$-$R^{53}$, respectively, comprises at least one anionic sulfonate, phosphonate, or a group containing a sulfonate or phosphonate group. In some other embodiments, $R^{31}$-$R^{34}$, $R^{41}$-$R^{44}$, and $R^{51}$-$R^{53}$ are independently alkyl groups and one of $R^{31}$-$R^{34}$, $R^{41}$-$R^{44}$, and $R^{51}$-$R^{53}$, respectively, is a sulfonate, phosphonate, or a group containing a sulfonate or phosphonate group.

In some embodiments, the zwitterionic compound in the disclosed column has a formula

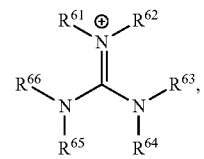

wherein $R^{61}$-$R^{66}$ are independently H, halogen, —NR'R", —NO$_2$, —COOR', —CHO, —OR', —PO$_3$R', —PO$_3$R'R", —SO$_2$, —SO$_3$R', —SR', substituted alkyl group, or unsubstituted alkyl group; wherein R' and R" are independently H or an alkyl group, and wherein at least one of $R^{61}$-$R^{66}$, respectively, comprises at least one anionic sulfonate, phosphonate, or a group containing —SO$_3^-$ or —P(OR$^6$)O$_2^-$ group; where $R^6$ is H or substituted or unsubstituted alkyl group (a sulfonate or phosphonate group). In some embodiments, the zwitterionic compound in the disclosed column is tetra-alkyl guanidinium compound (two of $R^{61}$-$R^{66}$ are Hs and four of $R^{61}$-$R^{66}$ are alkyl groups).

In some embodiments, the zwitterionic compound in the disclosed column is a neutral or charged. In some other embodiments, the zwitterionic compound is a liquid at a temperature between about 0° C. and 100° C. In some embodiments, the zwitterionic compound is a liquid at a temperature of room temperature, from about 10° C. to about 65° C., from about 20° C. to about 55° C., from about 30° C. to about 55° C., from about 30° C. to about 65° C., from about 40° C. to about 65° C., from about 40° C. to about 75° C., from about 60° C. to about 80° C., from about 80° C. to about 100° C., about 40° C., about 50° C., about 60° C., about 70° C., about 80° C., about 90° C., about 100° C., or any value there between.

In some embodiments, the zwitterionic compound in the disclosed column comprises two cationic systems. In some other embodiments, the zwitterionic compound comprises three or more cationic systems. In some other embodiments, the zwitterionic compound comprises one of a sulfonate, phosphonate, or a group containing a sulfonate or phosphonate group and one of a carboxylate, sulfonate, phosphonate, or a group containing a-sulfonate or phosphonate, or carboxylate group. In yet some other embodiments, the zwitterionic compound comprises one of a sulfonate, phosphonate, or a group containing a sulfonate or phosphonate group and two or more of a carboxylate, sulfonate, phosphonate, or a group containing a sulfonate or phosphonate, or carboxylate group.

In some embodiments, in addition to one cationic system, the zwitterionic compound in the disclosed column can have another one or more cationic systems. The multiple cationic systems in the zwitterionic compounds can be within the same substitute group or in different substitution groups. The additional anion group can be one or more of carboxylate, sulfonate, phosphonate, or a group containing a sulfonate or phosphonate, or carboxylate.

In some embodiments, in additional to one anionic sulfonate, phosphonate, or a group containing a sulfonate or phosphonate group, the zwitterionic compound in the disclosed column can have another one or more anionic groups. The multiple anionic groups in the zwitterionic compounds can be within the same substitution group or in different substitution groups.

In some embodiments, the zwitterionic compound in the disclosed column has a net positive charge by itself, the net positively charge(s) are balanced by external ion(s) with negative charge(s), such as $CH_3SO_3^-$, $Cl^-$, or other alkyl sulfonate. In some embodiments, the zwitterionic compound in the disclosed column has a net negative charge by itself, the net negative charge(s) are balanced by external ion(s) with positive charge(s).

In some embodiments, the zwitterionic compound in the disclosed gas chromatographic column has a formula:

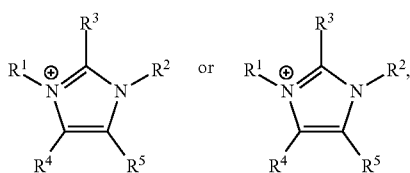

wherein both of $R^1$ and $R^2$ are alkyl sulfonate or phosphonate. In some other embodiments, $R^1$ is a nonionic alkyl group. In yet some other embodiments, $R^1$ is a nonionic alkyl group and $R^2$ is a sulfonate or phosphonate. In some embodiments, $R^1$ is a $C_1$-$C_{32}$ nonionic alkyl group and $R^2$ is an $C_1$-$C_{32}$ alkyl sulfonate, phosphonate, or a group containing a sulfonate or phosphonate. In some embodiments, one of $R^1$ and $R^2$ is a $C_1$-$C_{32}$ sulfonate, $C_1$-$C_{18}$ sulfonate, $C_1$-$C_{12}$ sulfonate, $C_1$-$C_6$ sulfonate, $C_3$-$C_{12}$ sulfonate, or $C_4$-$C_{10}$ sulfonate. In some other embodiments, at least one of $R^1$ and $R^2$ is a $C_1$-$C_{32}$ phosphonate, $C_1$-$C_{18}$ phosphonate, $C_1$-$C_{12}$ phosphonate, $C_1$-$C_6$ phosphonate, $C_3$-$C_{12}$ phosphonate, or $C_4$-$C_{10}$ phosphonate. In some other embodiments, at least one of $R^1$ and $R^2$ is a straight chain sulfonate or phosphonate, or straight chain alkyl containing a sulfonate or phosphonate group or anion thereof. In yet some other embodiments, at least one of $R^1$ and $R^2$ is a branched chain sulfonate or phosphonate, or a branched chain group containing a sulfonate or phosphonate group or anion thereof.

In some embodiments, $R^1$ is a $C_1$-$C_{20}$ alkyl group and $R^2$ is a sulfonate or phosphonate. In some other embodiments, $R^1$ is a $C_1$-$C_{20}$ unsubstituted alkyl group and $R^2$ is a sulfonate, phosphonate, or a group containing a-sulfonate or phosphonate group. In some other embodiments, $R^1$ is a $C_1$-$C_{20}$ unsubstituted and straight chain alkyl group and $R^2$ is a sulfonate, phosphonate, or group containing a sulfonate or phosphonate group. In some embodiments, $R^2$ is a sulfonate, phosphonate, or a group containing a sulfonate or phosphonate group; $R^1$ is a $R^7(OE)_nR^6$— group, $R^6$ is null, unsubstituted $C_1$-$C_{20}$ alkylene group, OE is —$OCH_2CH_2$—, —$OCH_2CH_2CH_2$—, —$OCH(CH_3)CH_2$—, or combination thereof, $R^7$ is H, —$CH_3$, —$CH_2CH_3$, or other unsubstituted or substituted alkyl group; and n is 1-50.

In some embodiments, $R^3$-$R^5$ are independently H, halogen, or $C_1$-$C_3$ unsubstituted alkyl group. In some other embodiments, $R^3$-$R^5$ are H.

In some embodiments, the zwitterionic compound in the disclosed column is

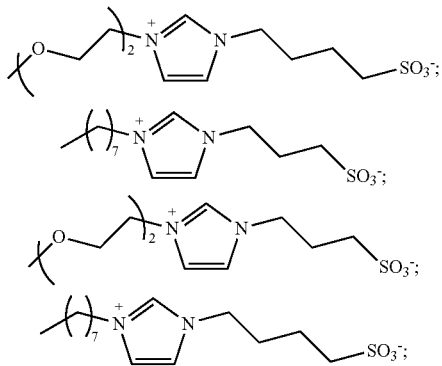

or a combination thereof.

In some embodiments, the column has a length of from about 0.5 m to 60 m. In some other embodiments, the column has a diameter of from 100 μm to about 560 μm. In yet some other embodiments, the column has a coating thickness of from 0.05 μm to 0.5 μm. In some other embodiments, the column is at a temperature of from about 0° C. to about 120° C.

In some embodiments, the column has a maximum allowable operating temperature (MAOT) of from about 150° C. to about 350° C., from about 200° C. to about 250° C., from about 250° C. to about 300° C., from about 300° C. to about 350° C., about 150° C., about 200° C., about 250° C., about 300° C., about 350° C., or any value there between.

In another aspect, disclosed herein is a method of chromatographic analysis or separation, the method comprises separating an analyte by a column; wherein the column comprises a zwitterionic compound disclosed herein as its stationary phase.

In some embodiments, the column used in the disclosed method herein is one of the gas chromatographic columns disclosed herein. In some other embodiments, the column is at a temperature from about 0° C. to about 120° C.

In some embodiments, the zwitterionic compound in the disclosed method is a molecule represented by a formula

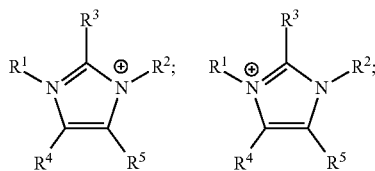

or mixture thereof, wherein $R^1$-$R^5$ are independently H, halogen, —NR'R", —$NO_2$, —COOR', —CHO, —OR', —$PO_3$H, —P($OR^6$)($OR^7$)O, —$SO_2$, $SO_3$H, —SR', or unsubstituted alkyl group; and wherein R', R", $R^6$, and $R^7$ are independently H or an alkyl group; and wherein at least one of $R^2$ and $R^1$ are independently sulfonate, phosphonate, or a group containing a sulfonate or phosphonate group or anion thereof.

In some embodiments, $R^1$ and $R^2$ are alkyl groups and at least one of $R^1$ and $R^2$ is a sulfonate or phosphonate. In some other embodiments, $R^1$ is a nonionic alkyl group and $R^2$ is a sulfonate or phosphonate. In some other embodiments, $R^1$ is a $C_1$-$C_{32}$ nonionic alkyl group and $R^2$ is a sulfonate. In some other embodiments, $R^1$ is a $C_1$-$C_{32}$ nonionic alkyl group, $R^2$ is a sulfonate, and $R^3$-$R^5$ are H.

In yet another aspect, disclosed herein is a method for GC analysis of a polar and volatile organic molecule, wherein the method comprises inputting a sample into a gas chromatographic column, wherein the column is one of the GC columns disclosed herein; and wherein the sample comprises a polar and volatile organic molecule.

In some embodiments, the zwitterionic compound has a formula

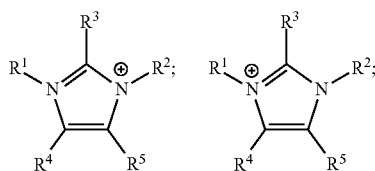

or mixture thereof, wherein $R^1$-$R^5$ are independently H, halogen, —NR'R", —$NO_2$, —COOR', —CHO, —OR', —$PO_3$R', —$PO_3$R'R", —$SO_2$, —$SO_3$R', —SR', or unsubstituted alkyl group; and wherein R' and R" are independently H or an alkyl group; wherein at least one of $R^2$ and $R^1$ are independently a sulfonate, phosphonate, or a group containing a sulfonate or phosphonate group.

In some embodiments, the organic molecule is not derivatized before the sample is input into the gas GC column. In some other embodiments, the organic molecule is a $C_1$-$C_{30}$, $C_1$-$C_{20}$, $C_1$-$C_{15}$, $C_1$-$C_{10}$, $C_1$-$C_6$ ester, alcohol, acid, ether, aldehyde, alkaloid, amine, or mixture thereof. In some other embodiments, the organic molecule is a $C_1$-$C_{30}$, $C_1$-$C_{20}$, $C_1$-$C_{15}$, $C_1$-$C_{10}$, $C_1$-$C_6$ free acid, or mixture thereof. In some embodiments, the organic molecule is volatile at room temperature or a temperature from about 0° C. to 50° C.

In some embodiments, $R^1$ and $R^2$ are alkyl groups and at least one of $R^1$ and $R^2$ is a sulfonate or phosphonate. In some other embodiments, $R^1$ is a $C_1$-$C_{32}$ nonionic alkyl group and $R^2$ is a sulfonate or phosphonate. In some other embodiments, $R^1$ is a $C_1$-$C_{32}$ nonionic alkyl group, $R^2$ is a sulfonate, and $R^3$-$R^5$ are H.

In some embodiments, the method disclosed herein for GC analysis further comprises detecting the organic molecule by FID, UV, or mass spectrometry (MS) measurement. In some embodiments, the method further comprises quantifying the concentration of the free acid in the sample based on the FID, UV, or MS measurement.

In some embodiments, the column has a length of from about 0.5 m to 60 m.

In some other embodiments, the column has a diameter of from 100 μm to about 560 μm.

In yet some other embodiments, the column has a coating thickness of from 0.05 μm to 0.5 μm.

In some other embodiments, the column is at a temperature of from about 0° C. to about 120° C.

In some embodiments, the column has a maximum allowable operating temperature (MAOT) of from about 150° C. to about 350° C., from about 200° C. to about 250° C., from about 250° C. to about 300° C., from about 300° C. to about 350° C., about 150° C., about 200° C., about 250° C., about 300° C., about 350° C., or any value there between.

All publications, patent applications, issued patents, and other documents referred to in this specification are indicative of the level of ordinary skill in the art to which this disclosure pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

EXAMPLES

Embodiments of the disclosed GC columns with zwitterionic compounds as stationary phase and methods of using thereof are further defined in the following non-limiting Examples. These Examples, while indicating certain embodiments of the GC columns and methods of use, are given by way of illustration only and should not be considered as limiting in any way. From the above discussion and these Examples, one skilled in the art can ascertain the essential characteristics of this disclosure, and without departing from the spirit and scope thereof, can make various changes and modifications of the embodiments of the disclosed GC columns and methods to adapt it to various usages and conditions. Thus, various modifications of the embodiments of the disclosed GC columns and methods, in addition to those shown and described herein, will be apparent to those skilled in the art from the foregoing description. Such modifications are also intended to fall within the scope of the appended claims.

Materials and Methods

Reagents and Materials

Butyraldehyde, ethyl acetate, and 2-nitrophenol were purchased from Acros Organics (Morris Plains, NJ, USA). Bromoethane and 1-butyl-3-methylimidazolium methanesulfonate was purchased from Alpha Aesar (Ward Hill, MA, USA). Ethyl benzene was purchased from Eastman Kodak Company (Rochester, NJ, USA). Benzene was purchased from EMD chemicals (Gibbstown, NJ, USA). Acetic acid, N,N-dimethylformamide and toluene were purchased from Fisher Scientific (Pittsburgh, PA, USA). Naphthalene, 2-chloroaniline, p-cresol, p-xylene, and 1-bromohexane were purchased from Fluka (Steinheim, Germany). Octylimidazole was purchased from IoLiTec (Heilbronn, Germany). Acetophenone, acrylic acid, aniline, acetonitrile, benzaldehyde, benzonitrile, benzyl alcohol, bromobutane, 1-bromooctane, bis[(trifluoromethyl)sulfonyl]imide, 1-butanol, 1,4-butanesultone, 1-chlorobutane, 1-chlorohexane, 1-chlorooctane, cyclohexanol, cyclohexanone, 1,2-dichlorobenzene, 1,4-dioxane, 1-decanol, formic acid, lactic acid, levulinic acid, methylimidazole, 1-iodobutane, iso-butyric acid, iso-hexanoic acid, iso-valeric acid, ethyl phenyl ether, methyl caproate, methacrylic acid, 1-nitropropane, n-butyric acid, n-hexanoic acid, n-heptanoic acid, n-octanoic acid, n-valeric acid 1-octanol, octylaldehyde, 1-pentanol, 2-pentanone, propionitrile, 1,3-propanesultone, dichloromethane, phenol, pyridine, pyrrole, m-xylene, o-xylene, 2-propanol, propionic acid and a standard mix containing ten volatile free acids were purchased from Sigma Aldrich (St. Louis, MO, USA). Untreated fused silica capillary (I.D. 250 μm) and a SLB IL-111 column (30 m×250 μm×0.20 μm) were obtained from Supelco (Bellefonte, PA, USA).

Instrumentation

All GC measurements used to characterize the stationary phases were performed on an Agilent 7890B instrument with a flame ionization detector (FID) or an Agilent 5977A mass spectrometry detector (MSD). Helium was used as the carrier gas with a flow rate of 1 mL/min. The inlet and FID detector temperatures were held at 250° C. A split ratio of 20:1 was used. The FID detector used hydrogen as a makeup gas at a flow rate of 30 mL/min and air flow was held at 400 mL/min.

Example 1

Preparation of Probe Solute Standards

The acid standards were prepared in acetonitrile at a concentration of 1 mg/mL. A standard mix of volatile acids was purchased from Sigma-Aldrich and were diluted to 300 ppm using acetonitrile. For experiments involving the solvation parameter model, a list of the 46 analytes and their corresponding solute descriptors is provided in Table 1. All probe molecules were dissolved in methylene chloride and injected individually at 3 different oven temperatures (50, 80, and 110° C.). Analytes possessing low boiling points exhibited low retention at higher temperatures whereas others exhibited very strong retention on the stationary phase (in some cases, beyond 3 hours). As a result, not all probe molecules could be subjected to regression analysis at the temperatures studied. Multiple linear regression analysis and statistical calculations were performed using the Analyze-it software (Leeds, UK).

TABLE 1

List of all probe molecules and their corresponding solute descriptors used to characterize metal-containing ionic liquid stationary phases employing the solvation parameter model

| Probe molecule | E | S | A | B | L |
| --- | --- | --- | --- | --- | --- |
| Acetic acid | 0.265 | 0.65 | 0.61 | 0.44 | 1.75 |
| Acetophenone | 0.818 | 1.01 | 0 | 0.48 | 4.501 |
| Aniline | 0.955 | 0.96 | 0.26 | 0.41 | 3.934 |
| Benzaldehyde | 0.82 | 1 | 0 | 0.39 | 4.008 |
| Benzene | 0.61 | 0.52 | 0 | 0.14 | 2.786 |
| Benzonitrile | 0.742 | 1.11 | 0 | 0.33 | 4.039 |
| Benzyl alcohol | 0.803 | 0.87 | 0.33 | 0.56 | 4.221 |
| Bromoethane | 0.366 | 0.4 | 0 | 0.12 | 2.62 |
| 1-Bromooctane | 0.339 | 0.4 | 0 | 0.12 | 5.09 |
| 1-Butanol | 0.224 | 0.42 | 0.37 | 0.48 | 2.601 |
| Butyraldehyde | 0.187 | 0.65 | 0 | 0.45 | 2.27 |
| 2-Chloroaniline | 1.033 | 0.92 | 0.25 | 0.31 | 4.674 |
| 1-Chlorobutane | 0.21 | 0.4 | 0 | 0.1 | 2.722 |
| 1-Chlorohexane | 0.201 | 0.4 | 0 | 0.1 | 3.777 |
| 1-Chlorooctane | 0.191 | 0.4 | 0 | 0.1 | 4.772 |
| p-Cresol | 0.82 | 0.87 | 0.57 | 0.31 | 4.312 |
| Cyclohexanol | 0.46 | 0.54 | 0.32 | 0.57 | 3.758 |
| Cyclohexanone | 0.403 | 0.86 | 0 | 0.56 | 3.792 |
| 1,2-Dichlorobenzene | 0.872 | 0.78 | 0 | 0.04 | 4.518 |
| N,N-Dimethylformamide | 0.367 | 1.31 | 0 | 0.74 | 3.173 |
| 1,4-Dioxane | 0.329 | 0.75 | 0 | 0.64 | 2.892 |
| Ethyl acetate | 0.106 | 0.62 | 0 | 0.45 | 2.314 |
| Ethyl benzene | 0.613 | 0.51 | 0 | 0.15 | 3.778 |
| 1-Iodobutane | 0.628 | 0.4 | 0 | 0.15 | 4.13 |
| Methyl caproate | 0.067 | 0.6 | 0 | 0.45 | 3.844 |
| Naphthalene | 1.34 | 0.92 | 0 | 0.2 | 5.161 |
| Nitrobenzene | 0.871 | 1.11 | 0 | 0.28 | 4.557 |
| 1-Nitropropane | 0.242 | 0.95 | 0 | 0.31 | 2.894 |
| 1-Octanol | 0.199 | 0.42 | 0.37 | 0.48 | 4.619 |
| Octylaldehyde | 0.16 | 0.65 | 0 | 0.45 | 4.361 |
| 1-Pentanol | 0.219 | 0.42 | 0.37 | 0.48 | 3.106 |
| 2-Pentanone | 0.143 | 0.68 | 0 | 0.51 | 2.755 |
| Ethyl phenyl ether | 0.681 | 0.7 | 0 | 0.32 | 4.242 |
| Phenol | 0.805 | 0.89 | 0.6 | 0.3 | 3.766 |
| Propionitrile | 0.162 | 0.9 | 0.02 | 0.36 | 2.082 |
| Pyridine | 0.631 | 0.84 | 0 | 0.52 | 3.022 |
| Pyrrole | 0.613 | 0.73 | 0.41 | 0.29 | 2.865 |
| Toluene | 0.601 | 0.52 | 0 | 0.14 | 3.325 |
| m-Xylene | 0.623 | 0.52 | 0 | 0.16 | 3.839 |
| o-Xylene | 0.663 | 0.56 | 0 | 0.16 | 3.939 |
| p-Xylene | 0.613 | 0.52 | 0 | 0.16 | 3.839 |
| 2-Propanol | 0.212 | 0.36 | 0.33 | 0.56 | 1.764 |
| 2-Nitrophenol | 1.015 | 1.05 | 0.05 | 0.37 | 4.76 |
| 1-Bromohexane | 0.349 | 0.4 | 0 | 0.12 | 4.13 |
| Propionic acid | 0.233 | 0.65 | 0.6 | 0.45 | 2.29 |
| 1-Decanol | 0.191 | 0.42 | 0.37 | 0.48 | 5.628 |

Example 2

Synthesis of Reference Ionic Liquids and Exemplary Zwitterionic Compounds

The structures of the exemplary zwitterionic compounds and reference ionic liquid compounds are shown in Table 2.

TABLE 2

Structures for the Exemplary Zwitterionic Compounds and Reference Ionic Liquid Compounds.

| Ref No. | Name | Structure |
|---|---|---|
| IL 1 | $OE_2IMC_4S$ | (structure) |
| IL 2 | $C_8IMC_3S$ | (structure) |
| IL 3 | $[OE_2PIM][MeSO_3]$ | (structure) |
| IL 4 | $C_8IMC_4S$ | (structure) |
| IL R1 | $([BMIM][NTf_2])$ | (structure) |
| IL R2 | $[BMIM][MeSO_3]$ | (structure) |

Synthetic procedures of the zwitterionic compounds reported in previously published papers (Kuroda, K.; Satria, H.; Miyamura, K.; Tsuge, Y.; Ninomiya, K.; Takahashi, K. *Journal of the American Chemical Society* 2017, 139, 16052-16055; Yoshizawa-Fujita, M.; Tamura, T.; Takeoka, Y.; Rikukawa, M. *Chemical Communications* 2011, 47, 2345-2347) were used for this Example. Briefly, 0.2 mol sodium hydride was suspended in tetrahydrofuran (THF) under argon gas. Imidazole (0.1 mol), which was dissolved in 30 mL THF, was added dropwise to the sodium hydride solution. After stirring for 24 h at room temperature, 1-bromo-2-(2-methoxyethoxy)ethane (0.1 mol) was added to the solution. The resulting suspension was filtered after stirring for 6 h at 70° C. to remove the white precipitate. The solvent was removed by rotary evaporation to yield the crude product. The product was further purified by distillation under reduced pressure. A fraction was collected at 105° C. under reduced pressure to obtain 1-(2-(2-methoxyethoxy) ethyl)-1H-imidazole ($OE_2im$). $OE_2im$ (0.1 mol) was subsequently dissolved in 40 mL acetonitrile. 1,4-butanesultone (0.1 mol) was added dropwise to the solution under a nitrogen atmosphere. The mixture was then refluxed for 40 h. The solvent was then removed by rotary evaporation. The residue was washed several times with diethyl ether by decantation followed by drying of the product under vacuum at 50° C. for 24 h to obtain IL 1, 3-(1-(2-Methoxyethyl)-1H-imidazol-3-ium-3-yl)butane-1-sulfonate ($OE_2imC_4S$) as a colorless viscous liquid. The zwitterionic compounds IL 2, 3-(1-octyl-1H-imidazol-3-ium-3-yl)propane-1-sulfonate ($C_8imC_3S$), and IL 4, 3-(1-octyl-1H-imidazol-3-ium-3-yl) butane-1-sulfonate ($C_8imC_4S$), were prepared in similar procedure using octylimidazole with 1,3-propanesultone or 1,4-butanesultone.

The IL R1 was synthesized using a previously published method. A mixture of 1-methylimidazole (0.05 mol) and 1-chlorobutane (0.075 mol) was added in 15 mL of isopropanol at 70° C. for 24 h. The solvent was removed using rotary evaporation. The product was then dissolved in 10 mL of water and washed using ethyl acetate (3 mL) for three times. The [BMIM][Cl] IL was recovered from the water layer and dried under vacuum at 80° C. for 24 h. The halide anion was then exchanged to $[BMIM][NTf_2]$ by metathesis reaction using one equivalent mole of $[Li][NTf_2]$.

$^1$H NMR data for the exemplary zwitterionic compounds and reference IL are provided below.

IL 1 ($OE_2IMC_4S$): 1H-NMR (400 MHz, DMSO-D6) δ 9.14 (s, 1H, NCHN), 7.77 and 7.71 (s, 2H, NCHCHN), 4.30 (t, J=4.8 Hz, 2H, $OCH_2CH_2N$), 4.17 (t, J=7.1 Hz, 2H, $NCH_2(CH_2)_3SO_3$), 3.73 (t, J=4.8 Hz, 2H, $OCH_2CH_2N$), 3.52-3.35 (m, 4H, $CH_3OCH_2CH_2$), 3.17 (s, 3H, $CH_3O$), 2.41 (t, J=7.6 Hz, 2H, $N(CH_2)_3CH_2SO_3$), 1.90-1.79 (m, 2H, $NCH_2CH_2(CH_2)_2SO_3$), 1.54-1.44 (m, 2H, $N(CH_2)_2CH_2CH_2SO_3$)

IL 2 ($C_8IMC_3S$): $^1$H NMR (500 MHz, DMSO-$d_6$) δ 9.18 (d, J=1.9 Hz, 1H), 7.79 (dt, J=9.1, 1.9 Hz, 2H), 4.30 (t, J=7.0 Hz, 2H), 4.15 (t, J=7.3 Hz, 2H), 2.39 (dd, J=8.5, 5.9 Hz, 2H), 2.09 (p, J=7.1 Hz, 2H), 1.85-1.64 (m, 2H), 1.25 (s, 9H), 0.86 (t, J=6.7 Hz, 3H).

IL 3 ($[OE_2IMC_3][MeSO_3]$): $^1$H NMR (500 MHz, DMSO-$d_6$) δ 9.21 (s, 1H), 7.80 (dt, J=18.7, 1.9 Hz, 2H), 4.36 (q, J=4.9 Hz, 2H), 4.16 (t, J=6.9 Hz, 2H), 3.77 (t, J=5.0 Hz, 2H), 3.54 (t, J=4.7 Hz, 2H), 3.40 (dd, J=5.7, 3.6 Hz, 2H), 2.32 (d, J=2.7 Hz, 3H), 1.81 (p, J=7.2 Hz, 2H), 0.84 (t, J=7.4 Hz, 3H).

IL 4 ($C_8IMC_4S$): $^1$H NMR (500 MHz, DMSO-$d_6$) δ 9.22 (s, 1H), 7.80 (d, J=1.7 Hz, 2H), 4.17 (dt, J=15.1, 7.1 Hz, 4H), 2.43 (d, J=7.6 Hz, 2H), 1.88 (p, J=7.2 Hz, 2H), 1.79 (t, J=7.2 Hz, 2H), 1.53 (p, J=7.7 Hz, 2H), 1.25 (d, J=9.5 Hz, 12H), 0.86 (t, J=6.7 Hz, 3H).

IL R1 ([BMIM][NTf$_2$]): $^1$H NMR (500 MHz, DMSO-d$_6$) δ 9.10 (s, 1H), 7.76 (t, J=1.8 Hz, 1H), 7.70 (t, J=1.8 Hz, 1H), 4.16 (t, J=7.2 Hz, 2H), 3.85 (s, 3H), 1.85-1.68 (m, 2H), 1.34-1.16 (m, 2H), 0.91 (t, J=7.4 Hz, 3H).

Example 3

Preparation of Exemplary Zwitterionic Compound-Based GC Columns and Reference IL-Based GC Column Five-meter untreated fused silica capillary columns were coated with the exemplary zwitterionic compounds or reference ionic liquids using the static coating method. The coated capillary columns were conditioned from 40-110° C. at 3° C./min and held for two hours. The column efficiency was determined using naphthalene at 100° C. A list of the prepared columns and their selected properties are shown in Table 3. No surface modification or deactivation process was used in the preparation of the columns.

TABLE 3

List of ionic liquids and zwitterionic compounds based stationary phases examined in this study

| IL No. | Abbreviation[a] | RTIL[a] | Solubility in Dichloromethane | Film Thickness (µm) | Efficiency (Plates/Meter)[c] |
|---|---|---|---|---|---|
| R1 | [BMIM][NTf$_2$] | Yes | Soluble | 0.28 | 2200 |
| R2 | [BMIM][MeSO$_3$] | No | Soluble | 0.28 | —[b] |
| 1 | OE$_2$IMC$_4$S | Yes | Suspended small liquid droplets | 0.20 | 1000 |
| 2 | C$_8$IMC$_3$S | Yes | Soluble | 0.20 | 2000 |
| 3 | [OE$_2$PIM][MeSO$_3$] | Yes | Soluble | 0.28 | —[b] |
| 4 | C$_8$IMC$_4$S | No | Soluble | 0.28 | —[b] |

[a]RTIL is abbreviation for room temperature ionic liquid.
[b]The efficiency values are lower than 1000 plates/meter.
[c]The column efficiency was determined by testing naphthalene at 100° C.

Example 4

Retention Behavior Of Free Acids on Exemplary Zwitterionic Compound-Based Columns and Reference Ionic Liquid-Based Columns To evaluate reference IL stationary phases possessing the methanesulfonate anion for the analysis of volatile free acids, two reference ILs, namely, IL R1 (1-butyl-3-methylimidazolium bis[(trifluoromethyl)sulfonyl]imide (BMIM NTf$_2$)) and IL R2 (1-butyl-3-methylimidazolium methanesulfonate (BMIM MeSO$_3$)), were selected. The NTf$_2$ anion within IL R1 has been widely used in commercial ionic liquid-based GC stationary phases, such as SLB-IL 59, SLB-IL100, and SLB-IL111. IL R2 shares the same cation (BMIM) as IL R1, but possesses the methanesulfonate anion (see Table 2). To examine the effect of methanesulfonate anion for the analysis of FAs, a volatile free acid mix containing ten volatile free acids (e.g. propionic acid, valeric acid, and heptanoic acid) were tested on the columns using IL R1 and IL R2 as stationary phases.

Figure 1B:
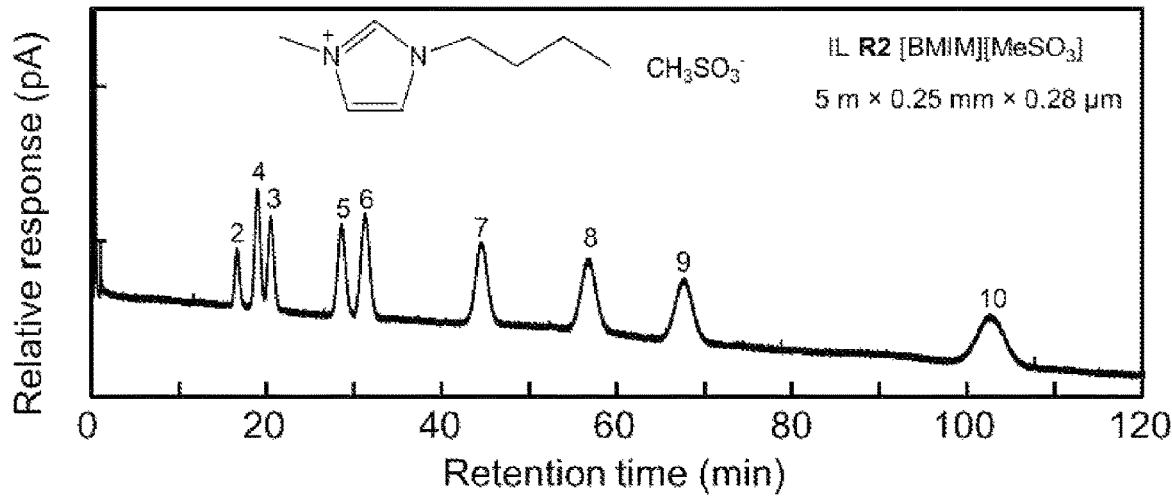
Figure 1C:
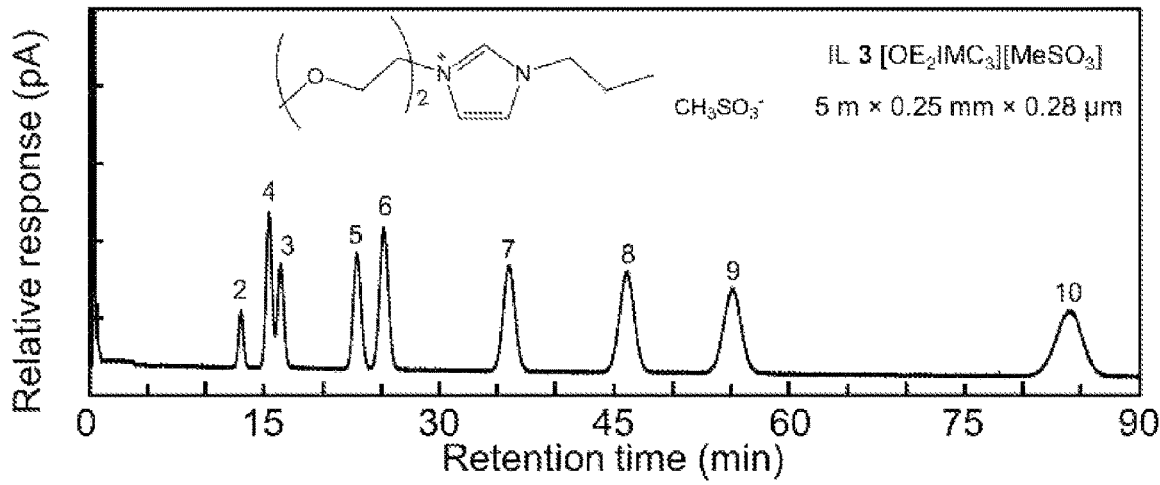

FIG. 1A, FIG. 1B, and FIG. 1C show chromatographic separations of volatile acid mixture by the columns with IL R1, IL R2, and IL 3, respectively. The analytes are: 1, formic acid; 2, acetic acid; 3, propionic acid; 4, iso-butyric acid; 5, n-butyric acid; 6, iso-valeric acid; 7, n-valeric acid; 8, iso-hexanoic acid; 9, n-hexanoic acid; 10, n-heptanoic acid. The formic acid was not observed on the chromatogram. All gas chromatography measurements were performed on an Agilent 7890B instrument with a flame ionization detector (FID). Helium was used as the carrier gas with a flow rate of 1 mL/min. The inlet and FID detector temperatures were held at 250° C. A split ratio of 20:1 was used. Five-meter columns with 250 µm inner diameter and 0.28 µm film thickness were used in this example. The FID detector used hydrogen as a makeup gas at a flow rate of 30 mL/min and air flow was held at 400 mL/min.

As shown in FIG. 1A, FIG. 1B, and FIG. 1C, all of the free acids were not strongly retained and eluted from the column within 6 min on the IL R1 based column. In addition, a number of analytes exhibited asymmetric peaks (e.g., n-hexanoic acid and n-heptanoic acid). In comparison, acids were observed to be strongly retained on the IL R2 column with good peak symmetry.

However, a major challenge was encountered while studying the robustness of the column with IL R2. As shown in the Table 4, a significant variation of the retention factor for the acids was observed when multiple injections of the free acids were subjected to the column with IL R2 (% RSD ranging from 6.79 to 11.31%), compared to one with IL R1 (% RSD ranging from 0.04% to 0.26%) (see Table 4). These results demonstrate that IL R2 is not suitable for the analysis of free acids. In addition, it is worth noting that the melting point of IL R2 is about 75 to 80° C. Due to the limited working range (minimum and maximum allowable operating temperature) of this compound, IL R2 (solid at room temperature) is not desirable as a stationary phase for gas-liquid chromatography. Our attention shifted to investigating structurally similar ILs that were liquids at room temperature and that were capable of retaining FAs with good peak symmetry while exhibiting very good retention time reproducibility.

As shown in Table 2, ILs 1, 2, and 4 are zwitterionic compounds possessing different side chain substituents. IL 3 is structurally similar to IL 1 except that it possesses the methanesulfonate anion. ILs 2 and 4 possess very similar structural features. Interestingly, IL 2 is a liquid at room temperature, while IL 4 is a solid. It has been previously reported that zwitterionic compounds with sulfonate or carboxylate functional group possess strong hydrogen bond basicity and were successfully used for the dissolution of cellulose. Fifteen free acids were prepared as standards and subjected to columns possessing ILs 1-4 as stationary phases and also to the commercial HP-FFAP column. As shown in Table 4, strong retention of acids was observed for the IL 1, 2, 3, 4, and R2 columns.

TABLE 4

Comparison of retention factors for selected free acids on six different zwitterion compound-based or ionic liquid-based stationary phases and commercial column at 100° C.

| Probe molecule | IL R1 | IL R2 | IL 1 | IL 2 |
|---|---|---|---|---|
| 1 formic acid | 0.98 ± 0.01 | —[a] | 65.28 ± 0.36 | 68.08 ± 0.15 |
| 2 acetic acid | 1.05 ± 0.01 | 51.96 ± 4.01 | 21.25 ± 0.06 | 29.27 ± 0.16 |

TABLE 4-continued

Comparison of retention factors for selected free acids on six different zwitterion compound-based or ionic liquid-based stationary phases and commercial column at 100° C.

| | | | | |
|---|---|---|---|---|
| 3 lactic acid | —[a] | —[a] | —[a] | —[a] |
| 4 acrylic acid | 2.01 ± 0.01 | 132.43 ± 14.98 | 50.05 ± 0.14 | 77.66 ± 0.30 |
| 5 propionic acid | 1.64 ± 0.01 | 62.94 ± 4.77 | 21.96 ± 0.14 | 42.87 ± 0.04 |
| 6 iso-butyric acid | 1.84 ± 0.01 | 57.75 ± 4.68 | 17.04 ± 0.08 | 44.42 ± 0.06 |
| 7 methacrylic acid | 2.55 ± 0.01 | 124.20 ± 11.06 | 38.89 ± 0.22 | 87.12 ± 0.13 |
| 8 n-butyric acid | 2.65 ± 0.01 | 86.20 ± 8.63 | 26.31 ± 0.06 | 67.91 ± 0.16 |
| 9 iso-valeric acid | 3.35 ± 0.01 | 94.51 ± 9.03 | 24.77 ± 0.02 | 83.13 ± 0.12 |
| 10 n-valeric acid | 4.57 ± 0.01 | 134.89 ± 13.47 | 36.06 ± 0.10 | 123.00 ± 0.29 |
| 11 iso-hexanoic acid | 6.49 ± 0.01 | 171.21 ± 17.77 | 39.99 ± 0.13 | 176.90 ± 0.36 |
| 12 n-hexanoic acid | 7.66 ± 0.01 | 202.99 ± 21.17 | 47.49 ± 0.08 | 215.27 ± 0.01 |
| 13 n-heptanoic acid | 12.77 ± 0.01 | 305.86 ± 34.53 | 62.23 ± 0.40 | 384.22 ± 0.43 |
| 14 n-octanoic acid | 20.98 ± 0.01 | 450.79 ± 30.67 | 82.23 ± 0.28 | 693.01 ± 0.29 |
| 15 levulinic acid | 170.23 ± 0.01 | —[a] | —[a] | —[a] |

| Probe molecule | HP-FFAP |
|---|---|
| 1 formic acid | 4.19 ± 0.01 |
| 2 acetic acid | 3.00 ± 0.01 |
| 3 lactic acid | 144.86 ± 0.02 |
| 4 acrylic acid | 8.29 ± 0.01 |
| 5 propionic acid | 4.92 ± 0.01 |
| 6 iso-butyric acid | 5.70 ± 0.01 |
| 7 methacrylic acid | 11.03 ± 0.01 |
| 8 n-butyric acid | 8.09 ± 0.01 |
| 9 iso-valeric acid | 10.27 ± 0.01 |
| 10 n-valeric acid | 15.09 ± 0.01 |
| 11 iso-hexanoic acid | 21.90 ± 0.01 |
| 12 n-hexanoic acid | 27.58 ± 0.03 |
| 13 n-heptanoic acid | 49.56 ± 0.01 |
| 14 n-octanoic acid | 88.65 ± 0.11 |
| 15 levulinic acid | 310.61 ± 0.13 |

[a]Note:
Compound did not elute or were not observable on the chromatogram. The column dimension for the IL 1 and IL 2 columns is 5 m × 0.25 mm × 0.2 μm, while the column dimension for the IL R1, and IL R2 columns is 5 m × 0.25 mm × 0.28 μm. A commercial column HP-FFAP (5 m × 0.25 mm × 0.25 μm) was used for comparison.

A comparison can first be made between ILs 1, 2, 3, 4 and the reference ILs R1 and R2. The retention behavior of free acids on ILs 1-4 is more comparable to IL R2, since they all share the same sulfonate functional group (see Tables 2 and 4). This result demonstrates that the sulfonate functional group plays an important role on the retention of fatty acids. It is important to note that the stability of the two zwitterionic compounds (% RSD of the retention factor ranging from 0.1% to 0.65%) is significantly better than that of IL R2 (% RSD ranging from 6.79% to 11.31%). When these zwitterionic compound-based stationary phases were compared to a widely used commercial column for the analysis of FAs (e.g., HP-FFAP), the retention factors of the acids were higher (see Table 4). Furthermore, the retention orders of analytes (e.g., acetic acid, propionic acid, and iso-butyric acid) on ILs 1 and 2 as well as the HP-FFAP column were vastly different. This result indicates that zwitterionic compound-based stationary phases can provide unique selectivity toward volatile free acids. It is important to note that lactic acid was observed to eluted only from the HP-FFAP column while levulinic acid was observed to elute the from the column with IL R1 and HP-FFAP column (see Table 4).

When evaluating the peak symmetry of free acids on the ionic liquid-based columns, tailing was observed for the late eluting compounds such as n-hexanoic acid and n-heptanoic acid on IL R1 as well as on SLB-IL111 column. To further evaluate the loading capacity and peak symmetry of free acids on these columns, a mixture containing five analytes (e.g., acetic acid, propionic acid, n-butyric acid, n-valeric acid, and n-hexanoic acid) at three different concentrations (100 ppm, 1 mg/mL, and 10 mg/mL) were examined on the three different columns. Table 5 compares the peak asymmetry factor of the volatile acids on four different columns (e.g., with IL 1, IL 2, SLB-IL111, and HP-FFAP columns, respectively). As shown in Table 5, IL 1 and IL 2 produced excellent peak symmetry at sample concentrations of 100 ppm and 1 mg/mL and were comparable to the HP-FFAP column.

TABLE 5

Peak asymmetry factors of five selected FAs on GC columns with the exemplary zwitterionic compounds and reference ionic liquids

| | | Peak Asymmetry Factor[b] | | |
|---|---|---|---|---|
| Column[a] | Probe Molecules | 100 ppm | 1 mg/mL | 10 mg/mL |
| IL 1 | acetic acid | 1.44 | 1.38 | 4.48 |
| 5 m × 0.25 mm × 0.2 μm | propionic acid | 1.22 | 1.31 | 2.74 |
| | butyric acid | 1.42 | 1.27 | 1.19 |
| | valeric acid | 1.53 | 1.35 | 0.80 |
| | hexanoic acid | 1.60 | 1.80 | 0.76 |
| IL 2 | acetic acid | 1.88 | 1.63 | 4.21 |
| 5 m × 0.25 mm × 0.2 μm | propionic acid | 1.52 | 1.47 | 3.70 |
| | butyric acid | 1.25 | 1.45 | 3.19 |
| | valeric acid | 1.34 | 1.38 | 2.94 |
| | hexanoic acid | 1.23 | 1.36 | 2.26 |
| SLB-IL111 | acetic acid | 2.10 | 6.15 | 5.44 |
| 5 m × 0.25 mm × 0.2 μm | propionic acid | 2.81 | 5.06 | 7.29 |
| | butyric acid | 2.59 | 4.87 | 4.95 |
| | valeric acid | 2.58 | 4.57 | 2.45 |
| | hexanoic acid | 2.63 | 3.69 | 2.03 |

TABLE 5-continued

Peak asymmetry factors of five selected FAs on GC columns with the exemplary zwitterionic compounds and reference ionic liquids

| Column[a] | Probe Molecules | Peak Asymmetry Factor[b] | | |
|---|---|---|---|---|
| | | 100 ppm | 1 mg/mL | 10 mg/mL |
| HP-FFAP | acetic acid | 1.11 | 1.57 | 7.64 |
| 5 m × 0.25 mm × 0.25 μm | propionic acid | 1.14 | 1.46 | 5.77 |
| | butyric acid | 1.09 | 1.33 | 4.01 |
| | valeric acid | 1.06 | 1.18 | 1.18 |
| | hexanoic acid | 1.06 | 1.00 | 0.67 |

[a]Note:
IL 1, OE$_2$IMC$_4$S; IL 2, C$_8$IMC$_3$S; SLB-IL111, 1,5-Di(2,3-dimethylimidazolium)pentane bis(trifluoromethanesulfonyl)imide.
[b]Note:
Peak asymmetry factors were measured using the ratio of right and left width from the peak leading edge to the peak midpoint at 10% of peak height.

Example 5

Separation of Free Acids on Zwitterionic Compound-Based GC Columns

The separation of an acid mix containing ten volatile acids was demonstrated on zwitterionic compound-based columns as well as a commercial HP-FFAP column in this example.

Figure 2A:
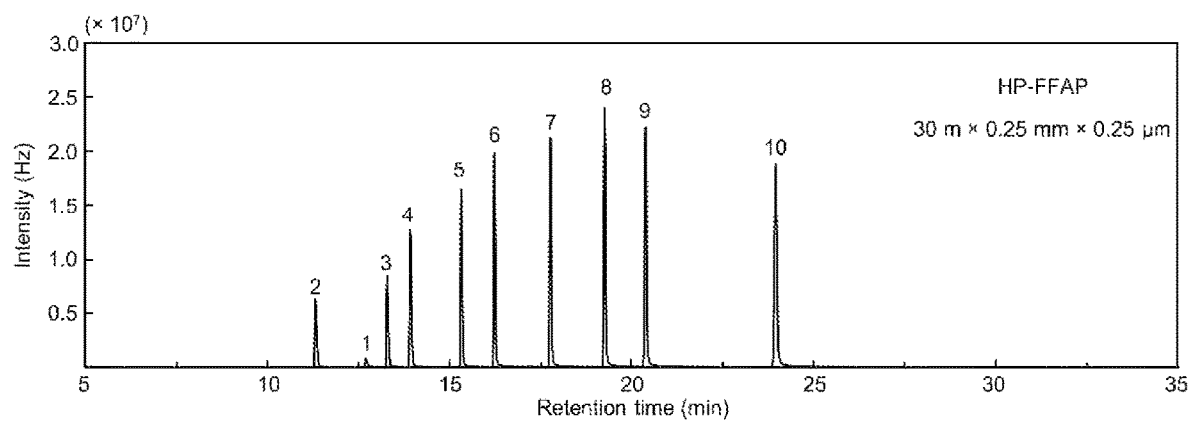
FIG. 2A, FIG. 2B, and FIG. 2C show chromatographic separations of a volatile acid mixture by HP-FFAP column, column with IL 1, and column with IL 2 using a mass spectrometry detector, respectively.
Figure 2B:
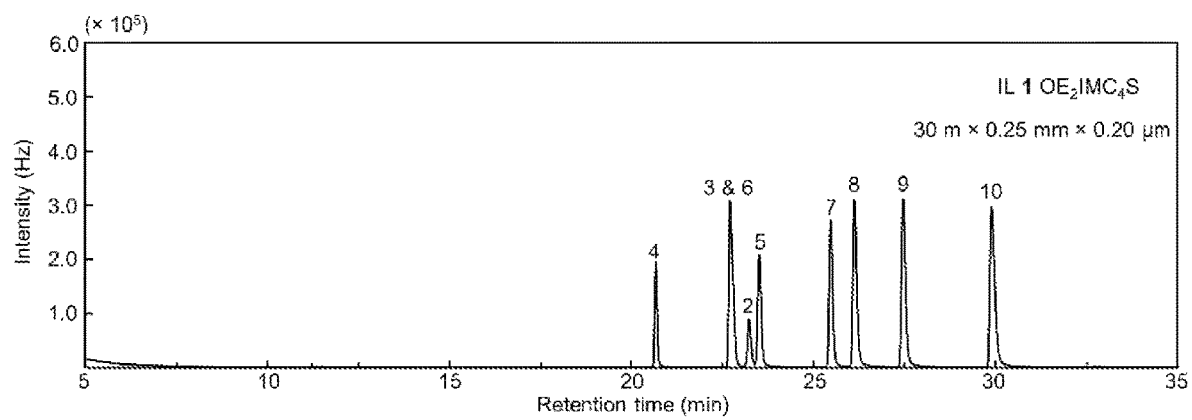
Figure 2C:
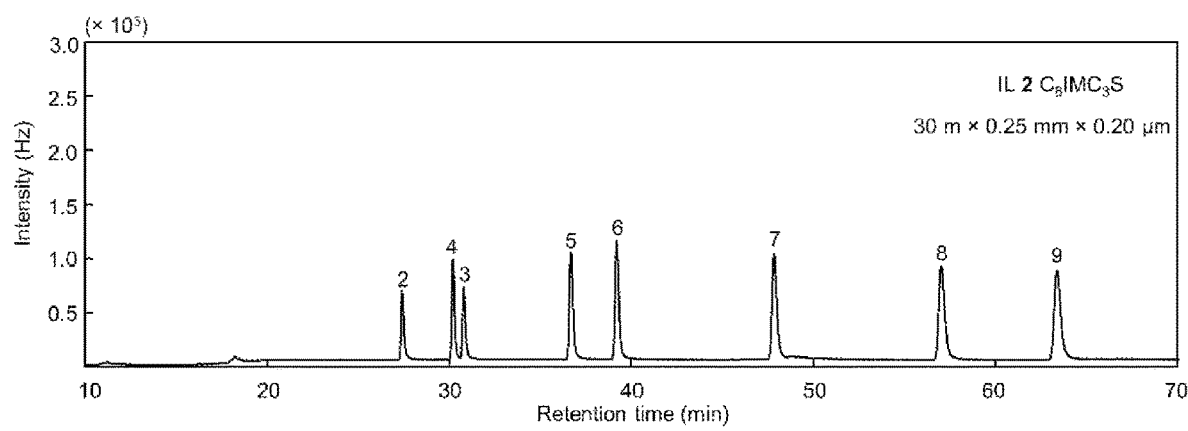

FIG. 2A, FIG. 2B, and FIG. 2C show chromatographic separations of a volatile acid mixture by HP-FFAP column, column with IL 1, and column with IL 2 using a mass spectrometry detector, respectively. The analytes are 1, formic acid; 2, acetic acid; 3, propionic acid; 4, iso-butyric acid; 5, n-butyric acid; 6, iso-valeric acid; 7, n-valeric acid; 8, iso-hexanoic acid; 9, n-hexanoic acid; 10, n-heptanoic acid. Helium was used as the carrier gas with a flow rate of 1 mL/min. The inlet temperature was held at 250° C. A split ratio of 20:1 was used. A temperature program was used: initial oven temperature, 60° C.; 5° C./min ramp to 150° C. and hold for 20 min for HP-FFAP and the column with IL 1 and 60 min for the column with IL 2. The mass spectrometer was operated in electron ionization mode (EI) at 70 eV for all analyses. Data were acquired in SCAN mode (mass range: 40-300 m/z). It was noted that formic acid was not observed on the columns with ILs 1 and 2. When the column with IL 2 column was used, n-heptanoic acid eluted after 80 min.

Free volatile acids retained strongly on the IL 1 and IL 2 columns. When the IL 1 and IL 2 columns (30 m×0.25 mm×0.2 μm) were compared with the commercial HP-FFAP column (30 m×0.25 mm×0.25 μm), the retention factors of all analytes were higher on the zwitterionic compound-based columns despite their thinner film thickness. Furthermore, unique separation selectivity on the zwitterionic compound-based columns was demonstrated. The retention order of several analytes including acetic acid, propionic acid, iso-butyric acid, n-butyric acid, and iso-valeric acid were different compared to the HP-FFAP column. In comparing the HP-FFAP column with IL 1 and IL 2, iso-butyric acid eluted first on the IL 1 column while the retention order of n-butyric acid and iso-valeric acid was also reversed on the IL 1 and IL 2 columns. When the columns with IL 1 and IL 3 were compared, the retention order of acetic acid and iso-butyric acid as well as n-butyric acid and iso-valeric acid were reversed (see FIG. 1A-FIG. 1C and FIG. 2A-FIG. 2C). This result indicates that the strong retention of iso-butyric acid versus propionic acid may be attributed to the higher dispersive-type interaction offered by IL 3. It is interesting to note that the retention order of free acids on the IL 3 column is more comparable to the IL 2 column instead of the IL 1 column (see FIG. 2A-FIG. 2C and FIG. 1A-FIG. 1C). In addition, the peak area and peak height for the volatile acids was much higher on the HP-FFAP column.

Example 6

Separation of Grob Mix on Zwitterionic Compound-Based Columns and Ionic Liquid-Based Columns To further evaluate these zwitterionic compound-based columns, the Grob Mix containing eleven different analytes was used.

Figure 3A:
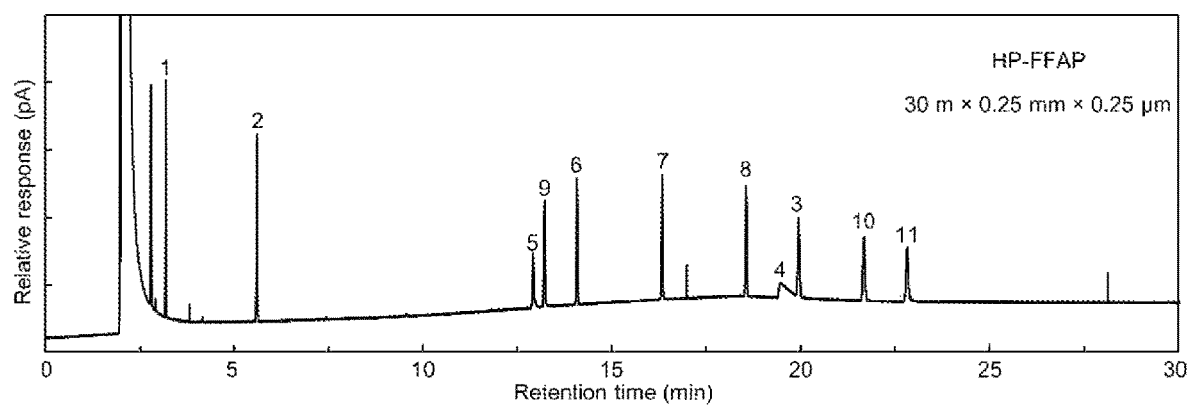
FIG. 3A, FIG. 3B, and FIG. 3C show chromatograms of the Grob Mix using a column with HP-FFAP; a column with IL 1; and a column with IL 2, respectively.
Figure 3B:
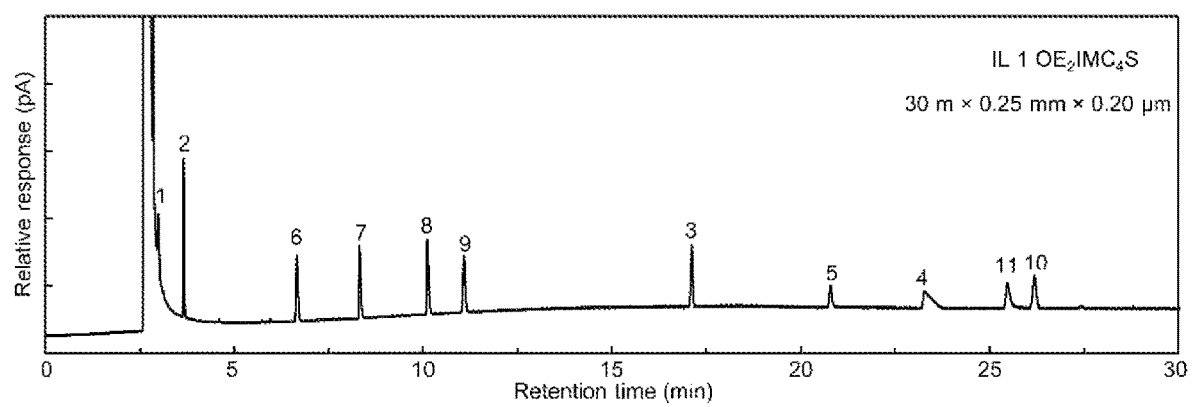
Figure 3C:
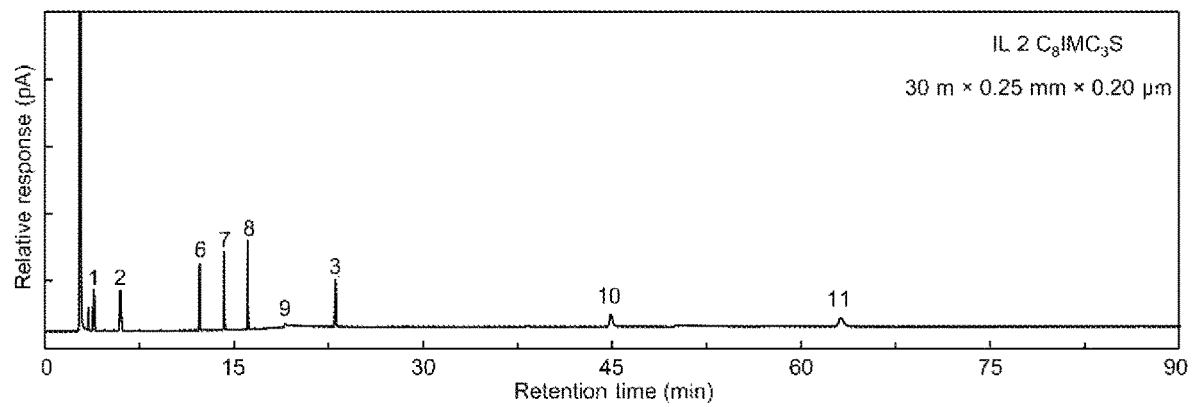

FIG. 3A, FIG. 3B, and FIG. 3C show GC chromatograms of the Grob Mix using a column with IL 1; column with IL 2; and HP-FFAP column, respectively. The analytes are: 1, decane; 2, dodecane; 3,2,6-dimethylaniline; 4, dicyclohexylamine; 5,2,3-butanediol; 6, methyl decanoate; 7, methyl undecanoate; 8, methyl laurate; 9,1-octanol; 10,2,6-dimethylphenol; 11,2-ethylhexanoic acid. All separations were performed using an Agilent 7890B with a flame ionization detector (FID). Helium was used as the carrier gas with a flow rate of 1 mL/min. A temperature program was used: initial oven temperature, 60° C.; 5° C./min ramp to 150° C. and hold for 20 min. The inlet and FID detector temperatures were held at 250° C. A split ratio of 20:1 was used. It was noted that Dicyclohexylamine and 2,3-butanediolwere not observed on the column with IL 2. The 1-octanol eluted out on the column with IL 2 as a strong tailing peak.

As shown in FIG. 3A, FIG. 3B, and FIG. 3C, three 30 m columns including IL 1 (30 m×0.25 mm×0.20 μm), IL 2 (30 m×0.25 mm×0.20 μm), and a HP-FFAP (30 m×0.25 mm×0.25 μm) were compared. The zwitterionic compound-based columns exhibited unique selectivity toward the various analytes. When IL 1 was compared to the HP-FFAP column, all eleven analytes eluted with excellent peak symmetry, with the exception of tailing peaks for dicyclohexylamine on both columns. Decane and dodecane eluted earlier on IL 1 compared to HP-FFAP. Interestingly, compared to the alkanes and fatty acid methyl esters (e.g., methyl decanoate and methyl undecanoate), the retention factors of 2,6-dimethylaniline, 2,3-butanediol, 2,6-dimethylphenol, and 2-ethylhexanoic acid were significantly increased. Furthermore, the retention order of several analyte pairs such as 1-octanol and 2,3-butanediol, 2,6-dimethylaniline and dicyclohexylamine, as well as 2,6-dimethylphenol and 2-ethylhexanoic acid were reversed on IL 1 and HP-FFAP columns as shown in FIG. 3B and FIG. 3A. Interestingly, the retention order of the 2,6-dimethylphenol and 2-ehtylhexanoic acid were reversed on the IL 1 and IL 2 columns as in FIG. 3B and FIG. 3C. These results demonstrate that the zwitterionic compound-based columns exhibit similar separation performance for the components within the Grob Mix, while providing unique selectivity toward alcohols and free acids.

Example 7

Solvation Properties of the Exemplary Zwitterionic Compounds and ILs

The Abraham solvation parameter model has been successfully utilized to characterize a wide range of ionic liquid-based GC stationary phases. This approach utilizes a linear free-energy relationship to describe the contribution of individual solvation interactions of a solvent (e.g., ionic liquid-based stationary phase) by evaluating solute/solvent interactions.

$$\text{Log } k = c + eE + sS + aA + bB + lL \quad (1)$$

As shown in the above equation, k represents the retention factor of each probe molecule on the stationary phase at a specific temperature. The solute descriptors are defined as: E, the excess molar refraction calculated from the solute's refractive index; S, the solute dipolarity/polarizability; A, the solute hydrogen bond acidity; B, the solute hydrogen bond basicity; and L, the solute gas hexadecane partition coefficient determined at 298 K. The solute descriptors E, S, A, B, and L have been previously determined and shown in Tables 1.

TABLE 6

A linear free-energy relationship was used in Abraham solvation parameter model to evaluate the solvation properties of zwitterionic compound and IL-based stationary phases
Log k = c + eE + sS + aA + bB + lL
k, retention factor of each probe molecule on the stationary phase at a specific temperature

| Unknown values representing the solvation properties of IL stationary phase | | Previously determined values of the probe molecules (see Table 1) |
|---|---|---|
| e | The ability of the stationary phase to interact with analytes by electron lone pair interactions | E | The excess molar refraction calculated from the solute's refractive index |
| s | A measure of the dipolarity/polarizability of the stationary phase | S | The solute dipolarity/polarizability |
| a | IL hydrogen bond basicity of the stationary phase | A | The solute hydrogen bond acidity |
| b | IL hydrogen bond acidity of the stationary phase | B | The solute hydrogen bond basicity |
| l | The dispersion forces/cavity formation of the IL | L | The solute gas hexadecane partition coefficient determined at 298K |
| c | The intercept of the regression line | | |

The c term represents the intercept of the regression line. The coefficients (e, s, a, b, and l) are the system constants used to characterize the strength of each solvation interaction. These system constants are defined as: e, the ability of the stationary phase to interact with analytes by electron lone pair interactions; s, a measure of the dipolarity/polarizability of the stationary phase; a and b, the IL hydrogen bond basicity and acidity of the stationary phase, respectively; and l describes the dispersion forces/cavity formation of the IL. System constants were determined for the exemplary zwitterionic compounds and reference ILs examined in this example at three different temperatures (50° C., 80° C., and 110° C.) and are listed in Table 7. The interactions between the probe molecules and the stationary phases become stronger at lower temperature, resulting in higher values of the system constants.

TABLE 7

System constants of the exemplary zwitterionic compounds and ionic liquids obtained by the solvation parameter model

| Stationary Phase | Temp (° C.) | System Constants | | | | | | | |
|---|---|---|---|---|---|---|---|---|---|
| | | c | e | s | a | b | l | n[a] | R²[a] | F[a] |
| DMIM NTf₂[b] | 50 | −2.90 | −0.21 | 1.71 | 1.97 | 0.26 | 0.72 | 39 | 0.99 | 549 |
| | | (0.09) | (0.08) | (0.10) | (0.08) | (0.12) | (0.02) | | | |
| | 80 | −2.91 | −0.06 | 1.62 | 1.62 | 0.19 | 0.60 | 38 | 0.99 | 691 |
| | | (0.07) | (0.06) | (0.08) | (0.06) | (0.10) | (0.01) | | | |
| | 110 | −2.98 | −0.07 | 1.56 | 1.36 | 0.11 | 0.52 | 36 | 0.99 | 632 |
| | | (0.06) | (0.05) | (0.07) | (0.06) | (0.09) | (0.01) | | | |
| IL 1 OE₂IMC₄S | 50 | −2.77 | 0.40 | 2.02 | 4.72 | −0.27 | 0.37 | 16 | 0.99 | 472 |
| | | (0.11) | (0.06) | (0.10) | (0.12) | (0.11) | (0.02) | | | |
| | 80 | −2.93 | 0.67 | 1.86 | 3.95 | −0.42 | 0.31 | 19 | 0.99 | 494 |
| | | (0.11) | (0.07) | (0.09) | (0.10) | (0.11) | (0.02) | | | |
| | 110 | −3.43 | 0.82 | 1.81 | 3.69 | 0.34 | 0.22 | 16 | 0.99 | 566 |
| | | (0.09) | (0.08) | (0.10) | (0.09) | (0.10) | (0.01) | | | |
| IL 2 C₈IMC₃S | 50 | −3.14 | 0.05 | 2.01 | 5.26 | −0.09 | 0.64 | 27 | 0.99 | 582 |
| | | (0.0) | (0.06) | (0.08) | (0.13) | (0.10) | (0.02) | | | |
| | 80 | −3.14 | 0.05 | 1.88 | 4.64 | −0.15 | 0.52 | 30 | 0.99 | 496 |
| | | (0.11) | (0.08) | (0.10) | (0.11) | (0.13) | (0.02) | | | |
| | 110 | −2.90 | 0.07 | 1.67 | 4.03 | −0.36 | 0.42 | 25 | 0.99 | 406 |
| | | (0.11) | (0.07) | (0.09) | (0.10) | (0.12) | (0.02) | | | |
| IL 3 [OE₂IMC₃] [MeSO₃] | 50 | −3.14 | 0.20 | 2.49 | 5.21 | 0 | 0.53 | 24 | 0.99 | 506 |
| | | (0.11) | (0.08) | (0.10) | (0.14) | (0.12) | (0.02) | | | |
| | 80 | −3.10 | 0.17 | 2.25 | 4.50 | −0.07 | 0.44 | 23 | 0.99 | 636 |
| | | (0.09) | (0.06) | (0.07) | (0.11) | (0.09) | (0.02) | | | |
| | 110 | −2.94 | 0.14 | 2.02 | 3.80 | −0.26 | 0.36 | 17 | 0.99 | 429 |
| | | (0.10) | (0.06) | (0.09) | (0.10) | (0.11) | (0.01) | | | |

TABLE 7-continued

System constants of the exemplary zwitterionic compounds and ionic liquids obtained by the solvation parameter model

| Stationary Phase | Temp (° C.) | c | e | s | a | b | l | n[a] | R²[a] | F[a] |
|---|---|---|---|---|---|---|---|---|---|---|
| IL 4 | 50 | —c | —c | —c | —c | —c | —c | —c | —c | —c |
| C$_8$IMC$_4$S | 80 | —c | —c | —c | —c | —c | —c | —c | —c | —c |
| | 110 | −3.25 (0.32) | 0.35 (0.17) | 1.84 (0.18) | 4.60 (0.24) | −0.79 (0.32) | 0.45 (0.03) | 10 | 0.99 | 92 |

[a] Note:
n, number of probe analytes subjected to multiple linear regression; R², correlation coefficient; F, Fisher coefficients.

[b] Note:
Data were obtained from a reference.

[c] Note:
Data were not able to be generated from the model due to a limited number of probe molecules were identified on 50° C. and 80° C. oven temperature.

The first comparison was made between 1-decyl-3-methylimidazolium bis[(trifluoromethyl)sulfonyl]imide (DMIM NTf$_2$) and IL 1, where IL 1 is a zwitterionic compound containing a PEG-based side chain. IL 1 possesses significantly higher hydrogen bond basicity value (a=3.95 at 80° C.) compared to the DMIM NTf$_2$ IL (a=1.62 at 80° C.). To further explore the solvation properties of these unique class of materials, IL 1 was compared to IL 2, which is a zwitterionic compound with an octyl side chain. IL 2 also possesses a high hydrogen bond basicity value (a=4.64, at 80° C.), which is even higher than a value of IL 1. In addition, IL 2 possess a high l term value (l=0.52, at 80° C.) compared to IL 1 (l=0.31, at 80° C.), indicating a stronger dispersive-type interaction toward analytes probes. IL 3 is structural homologue of IL 1. IL 3 also possesses high hydrogen bond basicity value (a=4.50, at 80° C.). Interestingly, IL 3 possess much higher l term value (l=0.44, at 80° C.) than IL 1 (l=0.31, at 80° C.). This can be attributed to the more accessible propyl side chain within IL 3 structure. IL 4 is a zwitterionic compound containing similar structural features as IL 2. The only difference is that IL 4 possesses a butyl side chain linker instead of propyl linker in IL 2. By comparing IL 1-IL 4 with DMIM NTf$_2$, one can conclude that the high hydrogen bond basicity values can be attributed to the sulfonate functional group. This result agrees with the reports that have shown tetra-n-butylammonium methanesulfonate (TBA MeSO$_3$) IL possesses higher a term value (a=3.76) than BMIM TfO and BMIM NTf$_2$ (see Table 8). It can be observed that IL 1-IL 4 possess strong hydrogen bonding basicity. These results agree with the observation of the chromatographic separation that the volatile acids (e.g., acetic acid and propionic acid) retained strongly on the columns with IL 1-IL 4 with good peak symmetry.

TABLE 8

System constants of ionic liquids obtained by the Solvation Parameter Model

| Stationary Phase | Temp (° C.) | c | e | s | a | b | l | n[a] | R²[a] | F[a] |
|---|---|---|---|---|---|---|---|---|---|---|
| BMIM NTf$_2$[b] | 40 | −2.87 | 0 | 1.89 | 2.02 | 0.36 | 0.63 | 33 | 0.99 | — |
| | 70 | −3.02 | 0 | 1.67 | 1.75 | 0.38 | 0.56 | 35 | 0.99 | — |
| | 110 | −3.13 | 0 | 1.60 | 1.55 | 0.24 | 0.49 | 32 | 0.98 | — |
| BMIM TfO[b] | 40 | −2.43 | 0 | 1.86 | 3.02 | 0 | 0.61 | 30 | 0.98 | — |
| | 70 | −2.64 | 0 | 1.73 | 2.71 | 0 | 0.52 | 31 | 0.99 | — |
| | 110 | −2.76 | 0 | 1.39 | 2.35 | 0 | 0.48 | 32 | 0.96 | — |
| TBA MeSO$_3$[c] | | −0.61 | 0.33 | 1.45 | 3.76 | — | 0.44 | — | 0.99 | — |
| DMIM NTf$_2$[d] | 50 | −2.90 (0.09) | −0.21 (0.08) | 1.71 (0.10) | 1.97 (0.08) | 0.26 (0.12) | 0.72 (0.02) | 39 | 0.99 | 549 |
| | 80 | −2.91 (0.07) | −0.06 (0.06) | 1.62 (0.08) | 1.62 (0.06) | 0.19 (0.10) | 0.60 (0.01) | 38 | 0.99 | 691 |
| | 110 | −2.98 (0.06) | −0.07 (0.05) | 1.56 (0.07) | 1.36 (0.06) | 0.11 (0.09) | 0.52 (0.01) | 36 | 0.99 | 632 |

[a] Note:
n, number of probe analytes subjected to multiple linear regression; R², correlation coefficient; F, Fisher coefficients.

bNote:
Data were obtained from a reference.

[c]TBA MeSO3, Tetra-n-butylammonium methanesulfonate. Data were obtained from a reference.

[d]Note:
Data were obtained from a reference.

Example 8

Thermal Stability of Some Exemplary Zwitterionic Compound-Based GC Columns

The maximum allowable operating temperature (MAOT) of the exemplary stationary phases were examined in this example. This was accomplished by heating the columns in the GC oven for 1 hour at different temperatures (e.g., 100°

C., 150° C., 200° C., and 250° C.) and recording the column bleed at these temperatures.

Figure 4A:
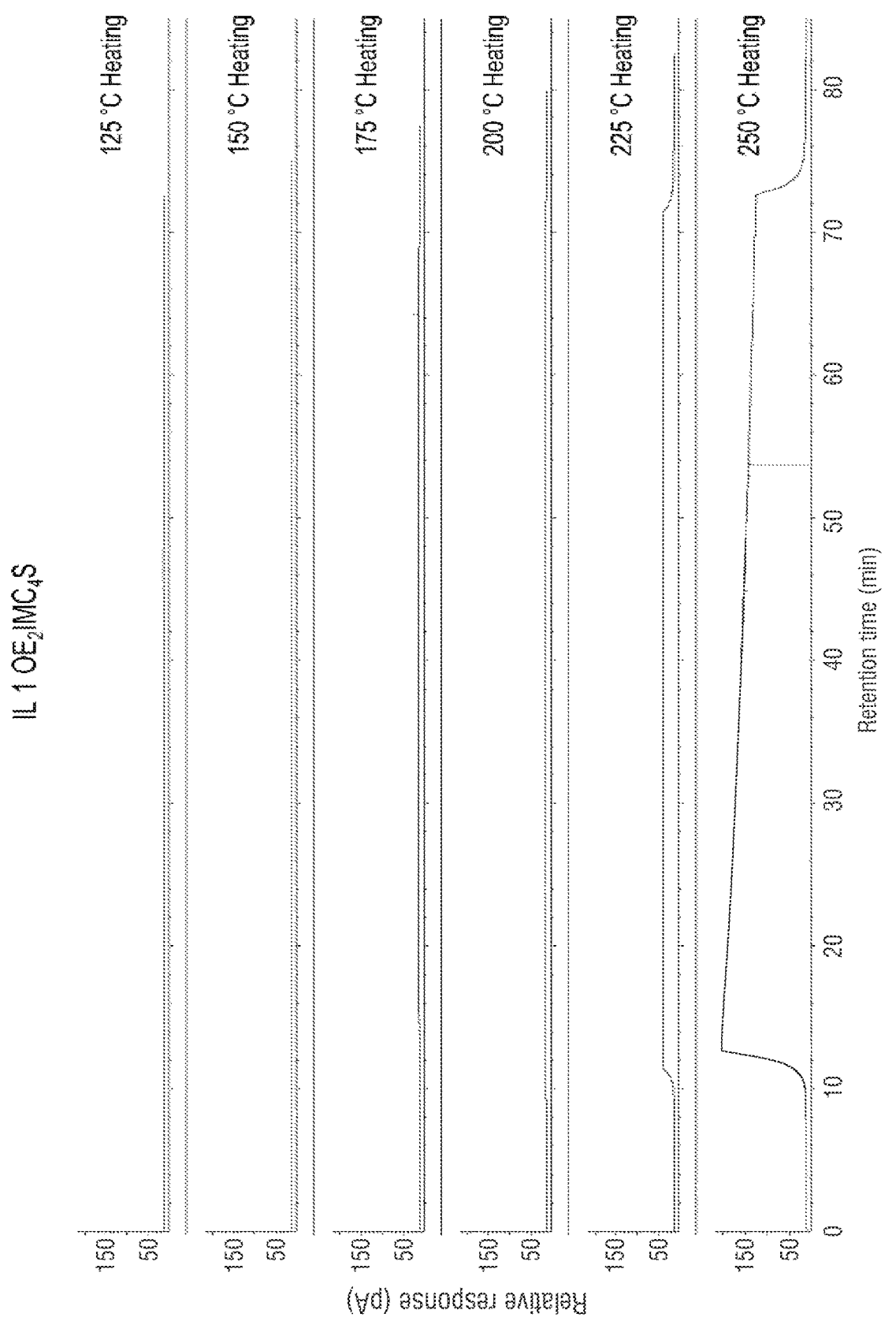
FIG. 4A and FIG. 4B show Column bleed profile and the column efficiency tests of the column with IL 1 after heating stepwise from 100° C. to 250° C., respectively.
Figure 4B:
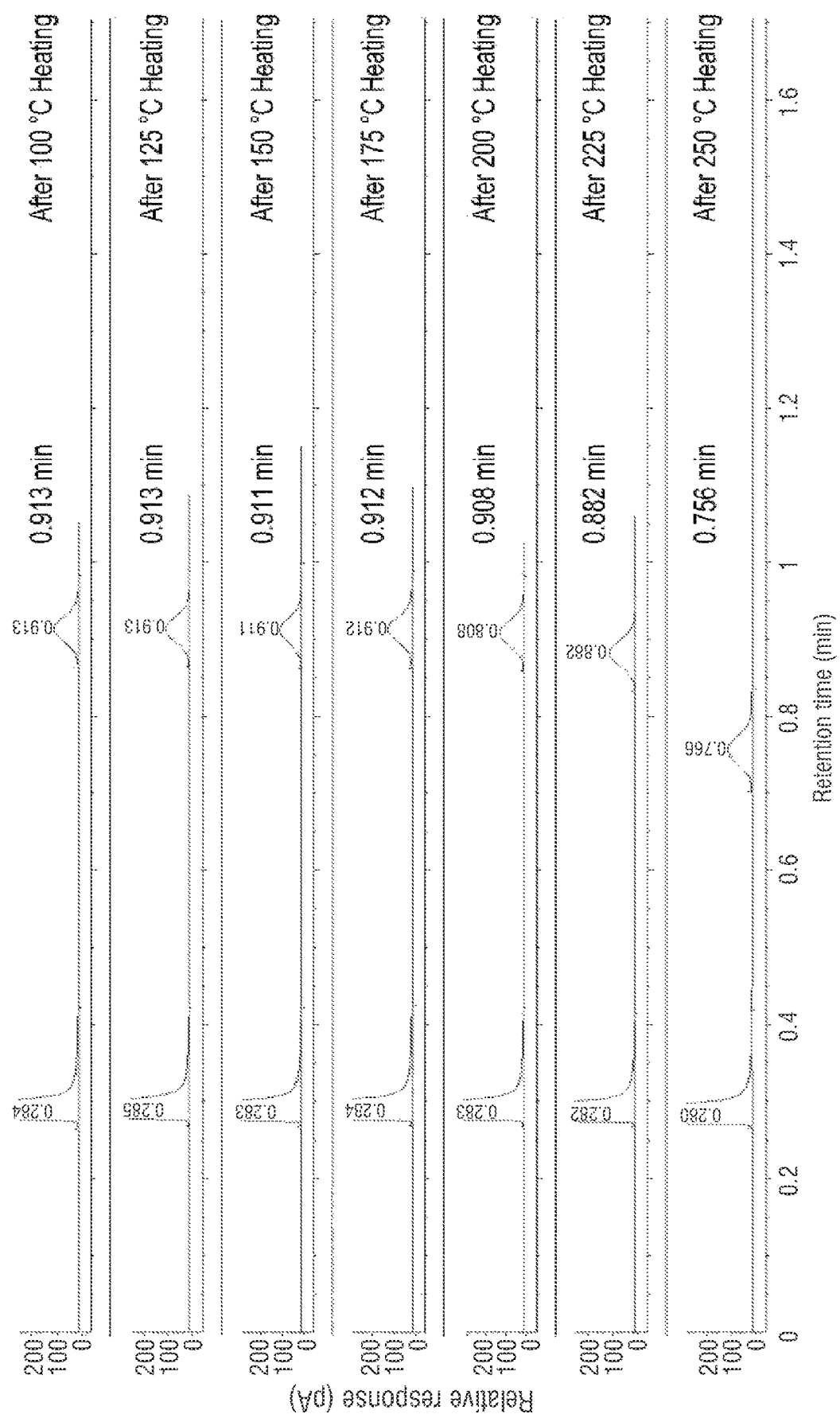

FIG. 4A and FIG. 4B show column bleed profile and the column efficiency tests of the column with IL 1 after heating stepwise from 100° C. to 250° C., respectively. The column bleed profile was generated by using a temperature program (100° C. hold for 5 min; 20° C./min heating up to a higher temperature ranging from 125° C. to 250° C. and hold for 1 hour; 20° C./min cooling down to 100° C.). The column efficiency test was performed after each heating step. The naphthalene standard solution (1 µL) was injected to the 5 m column at isothermal condition (100° C.) with a split ratio of 20:1. An Agilent 7890B system with a FID detector was used for the data collection.

As shown in the FIG. 4A, the column bleed profile revealed that significant column bleed was produced during heating up to 225° C. To further investigate the thermal stability of the column after each heating step, the GC oven was reset to 100° C. after each heating step and the column efficiency determined for naphthalene analysis. Since the column efficiency is dependent on the retention time and the peak width of the analyte, the MAOT could be determined by observing the significant change of the retention time or the peak width for the analyte. Also as shown in FIG. 4B, there was no observable change in the column efficiency until heating up to 225° C. However, after heating at 225° C. for 1 hour, a decrease in the retention time of naphthalene on the column with IL 1 was observed. After the column with IL 1 was heated to 250° C., a significant drop of the retention time and peak broadening was observed. Therefore, the MAOT of the column with IL 1 was found to be between 200° C. and 225° C.

Figure 5A:
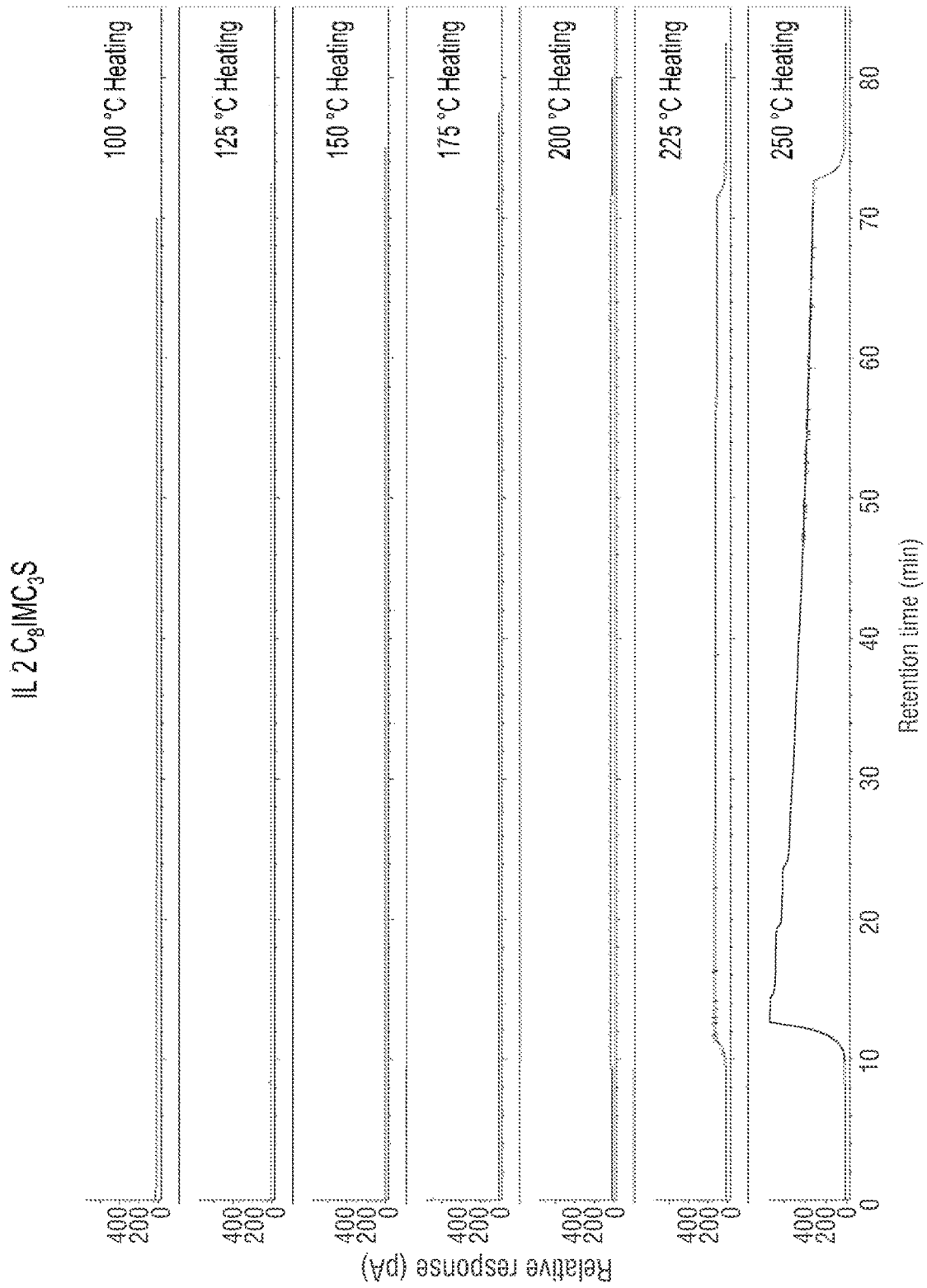
FIG. 5A and FIG. 5B show Column bleed profile and the column efficiency tests of the column with IL 2 after heating stepwise from 100° C. to 250° C., respectively.
Figure 5B:
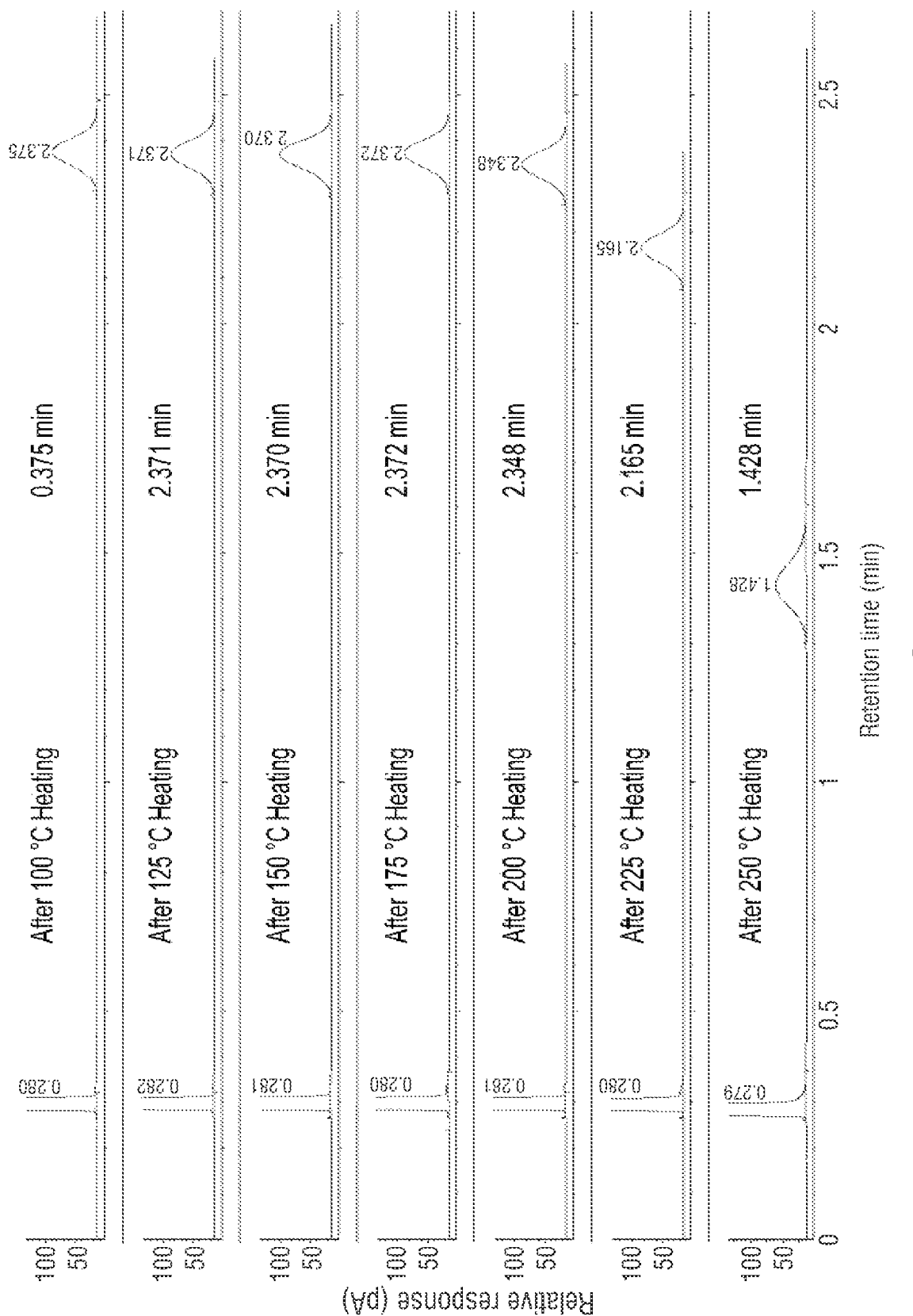

FIG. 5A and FIG. 5B show column bleed profile (A) and the column efficiency tests (B) of the column with IL 2 after heating stepwise from 100° C. to 250° C., respectively. The column bleed profile was generated by using a temperature program (100° C. hold for 5 min; 20° C./min heating up to a higher temperature ranging from 125° C. to 250° C. and hold for 1 hour; 20° C./min cooling down to 100° C.). The column efficiency test was performed after each heating step. The naphthalene standard solution (1 µL) was injected to the 5 m column at isothermal condition (100° C.) with a split ratio of 20:1. An Agilent 7890B system with an FID detector was used for the data collection.

As shown in FIG. 5A and FIG. 5B, the column with IL 2 exhibited a similar trend as one with IL 1. The retention time for naphthalene decreased after 225° C. heating. After heating at 250° C., a significant change of the column efficiency was observed. The MAOT of IL 2 was also determined to be between 200° C. and 225° C. After heating to 250° C., the column with IL 2 produced a significant decrease in the retention time and increase of the naphthalene peak width compared to the column with IL 1, indicating that IL 1 possesses higher thermal stability than IL 2.

The invention is being thus described. It will be obvious that the same may be varied in many ways. Such variations are not to be regarded as a departure from the spirit and scope of the present disclosure and all such modifications are intended to be included within the scope of the following claims.

What is claimed:

1. A method of chromatographic analysis or separation, the method comprises:
    separating an analyte by a column; wherein the column comprises a zwitterionic compound as its stationary phase,
    wherein the zwitterionic compound is a molecule represented by a formula:

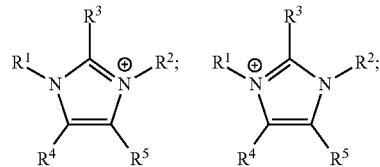

or mixture thereof,
   wherein $R^1$-$R^5$ are independently H, halogen, —NR'R", —NO$_2$, —COOR', —CHO, —OR', —PO$_3$H, —PO$_3$R', —PO$_3$R'R", —SO$_3$R', —SO$_2$, SO$_3$H, —SR', substituted alkyl group, or unsubstituted alkyl group; and wherein R' and R" are independently H or an alkyl group; and
   wherein at least one of $R^2$ and $R^1$ is a sulfonate or phosphonate, a group containing a —SO$_3$ or P(OR$^6$)O$_2^-$ group; where $R^6$ is H or substituted or unsubstituted alkyl group or anion thereof.

2. The method of claim 1, wherein the column is at a temperature from about 0° ° C. to about 120° C.

3. A method for gas chromatographic (GC) separation or analysis of an organic molecule, wherein the method comprises:
    inputting a sample into a gas chromatographic (GC) column,
    wherein the column comprises a zwitterionic compound as its stationary phase;
    wherein the zwitterionic compound is a molecule represented by a formula

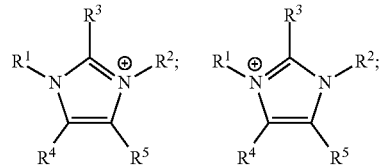

or mixture thereof,
   wherein $R^1$-$R^5$ are independently H, halogen, —NR'R", —NO$_2$, —COOR', —CHO, —OR', —PO$_3$R', —PO$_3$R'R", —SO$_2$, —SO$_3$R', —SR', or unsubstituted alkyl group; and wherein R' and R" are independently H or an alkyl group;
   wherein at least one of $R^2$ and $R^1$ is a sulfonate, phosphonate, or a group containing a —SO$_3$" or —P(OR$^6$)O$_2^-$ group; where $R^6$ is H, or substituted or unsubstituted alkyl group; or anion thereof; and
   wherein the sample comprises an organic molecule.

4. The method of claim 3, wherein the organic molecule is not derivatized before the sample is input into the GC column.

5. The method of claim 3, wherein the organic molecule is a $C_1$-$C_{30}$, $C_1$-$C_{20}$, $C_1$-$C_{15}$, $C_1$-$C_{10}$, $C_1$-$C_6$ ester, alcohol, free acid, ether, aldehyde, amine, or mixture thereof and is volatile at room temperature or a temperature from about 0° ° C. to 50° C.

6. The method of claim 3, the method further comprises detecting or quantifying the organic molecule by FID, UV, or mass spectrometry (MS) measurement.

7. The method of claim 3, wherein the gas chromatographic (GC) column has a length of from about 0.5 m to 60 m, a diameter of from 100 μm to about 560 μm, and a coating thickness of from 0.05 μm to 0.5 μm.

8. The method of claim 3, wherein the GC column is at a temperature of from about 0° ° C. to about 120° C.

* * * * *